US008687925B2

(12) United States Patent
Sano et al.

(10) Patent No.: US 8,687,925 B2
(45) Date of Patent: Apr. 1, 2014

(54) IMAGE STORAGE PROCESSING APPARATUS, IMAGE SEARCH APPARATUS, IMAGE STORAGE PROCESSING METHOD, IMAGE SEARCH METHOD AND PROGRAM

(75) Inventors: Akane Sano, Tokyo (JP); Masaaki Tsuruta, Tokyo (JP); Nozomu Ozaki, Kanagawa (JP); Masamichi Asukai, Kanagawa (JP); Taiji Ito, Kanagawa (JP); Akinobu Sugino, Kanagawa (JP); Hidehiko Sekizawa, Tokyo (JP); Yoichiro Sako, Tokyo (JP); Hideko Tabata, Tokyo (JP)

(73) Assignee: Sony Corporation, Tokyo (JP)

( * ) Notice: Subject to any disclaimer, the term of this patent is extended or adjusted under 35 U.S.C. 154(b) by 1096 days.

(21) Appl. No.: 12/080,932

(22) Filed: Apr. 7, 2008

(65) Prior Publication Data

US 2008/0253695 A1 Oct. 16, 2008

(30) Foreign Application Priority Data

Apr. 10, 2007 (JP) .................................. 2007-102659

(51) Int. Cl.
| | |
|---|---|
| G06K 9/54 | (2006.01) |
| G06K 9/62 | (2006.01) |
| G06K 7/00 | (2006.01) |
| A61M 21/00 | (2006.01) |
| G06F 12/00 | (2006.01) |
| H04H 60/56 | (2008.01) |

(52) U.S. Cl.
USPC ........... 382/305; 382/160; 382/312; 707/825; 707/830; 600/27; 725/12

(58) Field of Classification Search
USPC .......... 382/115, 305, 160, 312; 707/825, 830; 600/27; 725/12
See application file for complete search history.

(56) References Cited

U.S. PATENT DOCUMENTS

| | | | | |
|---|---|---|---|---|
| 5,781,650 A | * | 7/1998 | Lobo et al. | .................... 382/118 |
| 6,072,496 A | | 6/2000 | Guenter et al. | |

(Continued)

FOREIGN PATENT DOCUMENTS

| | | |
|---|---|---|
| CN | 1605974 A | 4/2005 |
| CN | 1835711 A | 9/2006 |

(Continued)

OTHER PUBLICATIONS

Healey, Jennifer et al.: "StartleCam: A Cybernetic Wearable Camera,". Digest of Papers. Second International Symposium on Wearable Computers, 1998 Pittsburgh, PA USA Oct. 19-20, 1998, pp. 42-49.

*Primary Examiner* — Kathleen Y Dulaney
(74) *Attorney, Agent, or Firm* — Wolf, Greenfield & Sacks, P.C.

(57) ABSTRACT

An image storage processing apparatus includes an image acquisition means for acquiring taken image data imaged at an imaging apparatus unit, a bio-information acquisition means for acquiring bio-information of a user of the imaging apparatus unit at the time of imaging the taken image data acquired by the image acquisition means, a subject information acquisition means for acquiring subject information as an image analysis result of the taken image data acquired by the image acquisition means and a storage processing means for performing processing of recording the taken image data acquired by the image acquisition means, the bio-information acquired by the bio-information acquisition means and the subject information acquired by the subject information acquisition means in a recording medium in a state in which they are associated with one another.

22 Claims, 13 Drawing Sheets

(56) References Cited

U.S. PATENT DOCUMENTS

| | | | |
|---|---|---|---|
| 6,091,546 A | 7/2000 | Spitzer | |
| 6,181,371 B1 | 1/2001 | Maguire, Jr. | |
| 6,272,231 B1 | 8/2001 | Maurer et al. | |
| 6,293,904 B1* | 9/2001 | Blazey et al. | 600/26 |
| 6,362,817 B1 | 3/2002 | Powers et al. | |
| 6,466,862 B1 | 10/2002 | Dekock et al. | |
| 6,549,231 B1 | 4/2003 | Matsui | |
| 6,549,913 B1* | 4/2003 | Murakawa | 1/1 |
| 6,585,521 B1* | 7/2003 | Obrador | 434/236 |
| 6,629,104 B1* | 9/2003 | Parulski et al. | 382/307 |
| 6,774,885 B1 | 8/2004 | Even-Zohar | |
| 7,085,648 B2 | 8/2006 | Ishiguro | |
| 7,183,909 B2 | 2/2007 | Miyajima | |
| 7,286,753 B2 | 10/2007 | Yamasaki | |
| 7,876,374 B2* | 1/2011 | Sako et al. | 348/333.01 |
| 8,009,219 B2 | 8/2011 | Sako et al. | |
| 8,126,220 B2* | 2/2012 | Greig | 382/118 |
| 8,473,544 B2 | 6/2013 | Sako et al. | |
| 2001/0005230 A1 | 6/2001 | Ishikawa | |
| 2001/0040590 A1 | 11/2001 | Abbott et al. | |
| 2002/0007105 A1* | 1/2002 | Prabhu et al. | 600/26 |
| 2002/0054174 A1 | 5/2002 | Abbott et al. | |
| 2002/0101619 A1* | 8/2002 | Tsubaki et al. | 358/302 |
| 2002/0128541 A1 | 9/2002 | Kim et al. | |
| 2003/0009078 A1* | 1/2003 | Fedorovskaya et al. | 600/26 |
| 2003/0011684 A1 | 1/2003 | Narayanaswami et al. | |
| 2003/0117505 A1 | 6/2003 | Sasaki et al. | |
| 2003/0118974 A1* | 6/2003 | Obrador | 434/236 |
| 2003/0128389 A1* | 7/2003 | Matraszek et al. | 358/1.18 |
| 2003/0165270 A1* | 9/2003 | Endrikhovski et al. | 382/189 |
| 2003/0225516 A1 | 12/2003 | DeKock et al. | |
| 2003/0235411 A1 | 12/2003 | Morikawa et al. | |
| 2004/0101178 A1* | 5/2004 | Fedorovskaya et al. | 382/128 |
| 2004/0101212 A1* | 5/2004 | Fedorovskaya et al. | 382/305 |
| 2004/0174443 A1 | 9/2004 | Simske | |
| 2004/0201692 A1* | 10/2004 | Parulski et al. | 348/207.1 |
| 2004/0210661 A1* | 10/2004 | Thompson | 709/228 |
| 2004/0221224 A1 | 11/2004 | Blattner et al. | |
| 2004/0243567 A1* | 12/2004 | Levy | 707/3 |
| 2004/0267440 A1 | 12/2004 | Dekock et al. | |
| 2005/0054381 A1 | 3/2005 | Lee et al. | |
| 2005/0083333 A1 | 4/2005 | Gordon | |
| 2005/0088297 A1* | 4/2005 | Miyajima | 340/539.12 |
| 2005/0124851 A1* | 6/2005 | Patton et al. | 600/26 |
| 2005/0171997 A1 | 8/2005 | Seo et al. | |
| 2005/0181347 A1 | 8/2005 | Barnes et al. | |
| 2005/0195277 A1 | 9/2005 | Yamasaki | |
| 2005/0206583 A1 | 9/2005 | Lemelson et al. | |
| 2005/0248469 A1 | 11/2005 | Dekock et al. | |
| 2005/0248852 A1 | 11/2005 | Yamasaki | |
| 2005/0250996 A1* | 11/2005 | Shirai et al. | 600/301 |
| 2005/0289582 A1* | 12/2005 | Tavares et al. | 725/10 |
| 2006/0010240 A1 | 1/2006 | Chuah | |
| 2006/0012690 A1 | 1/2006 | Nakamura et al. | |
| 2006/0074546 A1 | 4/2006 | Dekock et al. | |
| 2006/0115130 A1 | 6/2006 | Kozlay | |
| 2006/0134585 A1 | 6/2006 | Adamo-Villani et al. | |
| 2006/0143647 A1* | 6/2006 | Bill | 725/10 |
| 2006/0217598 A1 | 9/2006 | Miyajima et al. | |
| 2006/0256382 A1* | 11/2006 | Matraszek et al. | 358/1.18 |
| 2007/0067273 A1* | 3/2007 | Willcock | 707/4 |
| 2007/0074114 A1 | 3/2007 | Adjali et al. | |
| 2007/0113181 A1 | 5/2007 | Blattner et al. | |
| 2007/0132765 A1 | 6/2007 | Lee et al. | |
| 2007/0172155 A1* | 7/2007 | Guckenberger | 382/305 |
| 2007/0201767 A1* | 8/2007 | Fujita | 382/305 |
| 2007/0285560 A1 | 12/2007 | Perlman | |
| 2008/0020361 A1 | 1/2008 | Kron et al. | |
| 2008/0045804 A1 | 2/2008 | Williams | |
| 2008/0052242 A1 | 2/2008 | Merritt et al. | |
| 2008/0091512 A1* | 4/2008 | Marci et al. | 705/10 |
| 2008/0107361 A1* | 5/2008 | Asukai et al. | 382/317 |
| 2008/0129839 A1 | 6/2008 | Asukai | |
| 2008/0136930 A1 | 6/2008 | Nagai | |
| 2008/0146302 A1 | 6/2008 | Olsen et al. | |
| 2008/0158232 A1 | 7/2008 | Shuster | |
| 2008/0181513 A1* | 7/2008 | Almeida | 382/224 |
| 2008/0187186 A1* | 8/2008 | Togashi | 382/118 |
| 2008/0215974 A1 | 9/2008 | Harrison et al. | |
| 2008/0259199 A1 | 10/2008 | Sako et al. | |
| 2008/0273765 A1* | 11/2008 | Tsujimura | 382/118 |
| 2009/0040231 A1 | 2/2009 | Sano et al. | |
| 2009/0124922 A1* | 5/2009 | Milgramm et al. | 600/544 |
| 2009/0279792 A1* | 11/2009 | Obdrzalek et al. | 382/224 |

FOREIGN PATENT DOCUMENTS

| | | |
|---|---|---|
| EP | 1246136 A2 | 3/2002 |
| EP | 1 324 274 A2 | 7/2003 |
| EP | 1324274 A | 7/2003 |
| EP | 1503376 A2 | 2/2005 |
| EP | 1571634 A1 | 2/2005 |
| EP | 1522256 A1 | 4/2005 |
| EP | 1593964 A1 | 11/2005 |
| EP | 1656880 A | 5/2006 |
| EP | 1708150 A | 10/2006 |
| GB | 2394852 A | 5/2004 |
| GB | 2403366 A | 12/2004 |
| JP | 09-065188 A | 3/1997 |
| JP | 10-113343 A | 5/1998 |
| JP | 2002-169809 A | 6/2002 |
| JP | 2003-079591 A | 3/2003 |
| JP | 2004-049309 A | 2/2004 |
| JP | 2004-178593 | 6/2004 |
| JP | 2004-194996 A | 7/2004 |
| JP | 2004-537193 A | 12/2004 |
| JP | 2004-538679 A | 12/2004 |
| JP | 2004-538681 A | 12/2004 |
| JP | 2005-064839 A | 3/2005 |
| JP | 2005-124909 | 5/2005 |
| JP | 2005-141281 | 6/2005 |
| JP | 2005-172851 A | 6/2005 |
| JP | 2005-195425 A | 7/2005 |
| JP | 2005-250977 | 9/2005 |
| JP | 2005-260892 | 9/2005 |
| JP | 2005-337863 A | 12/2005 |
| JP | 2005-341604 A | 12/2005 |
| JP | 2006-034803 A | 2/2006 |
| JP | 2006-080644 A | 3/2006 |
| JP | 2006-086823 A | 3/2006 |
| JP | 2006-087829 A | 4/2006 |
| JP | 2006-126891 A | 5/2006 |
| JP | 2006-146630 A | 6/2006 |
| JP | 2006-172146 A | 6/2006 |
| JP | 2007-011391 A | 1/2007 |
| JP | 2007-041964 A | 2/2007 |
| JP | 2007-081681 A | 3/2007 |
| WO | WO 99/49656 A1 | 9/1999 |
| WO | WO 01/43104 A1 | 6/2001 |
| WO | WO 2004/017249 A2 | 2/2004 |

* cited by examiner

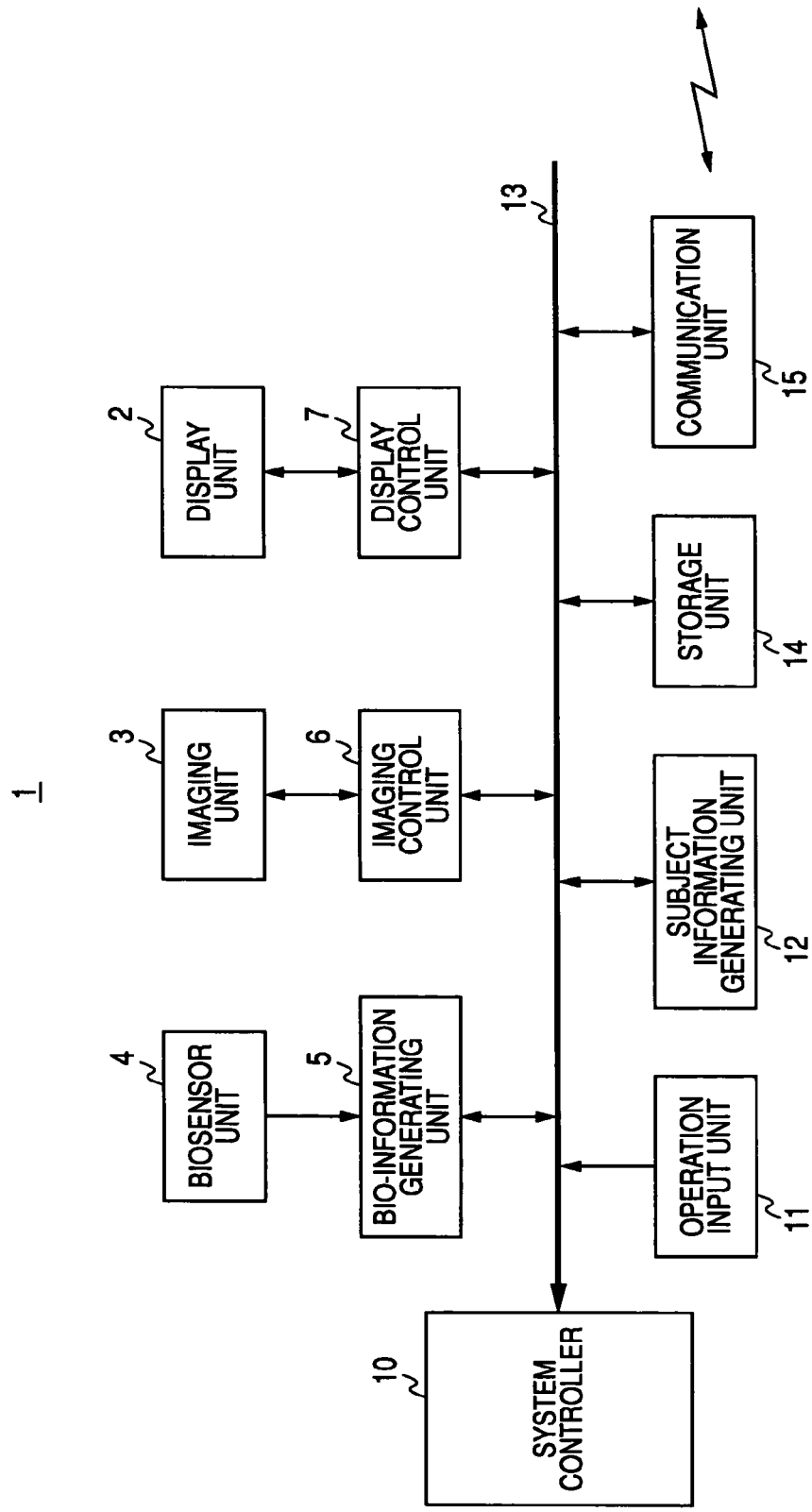

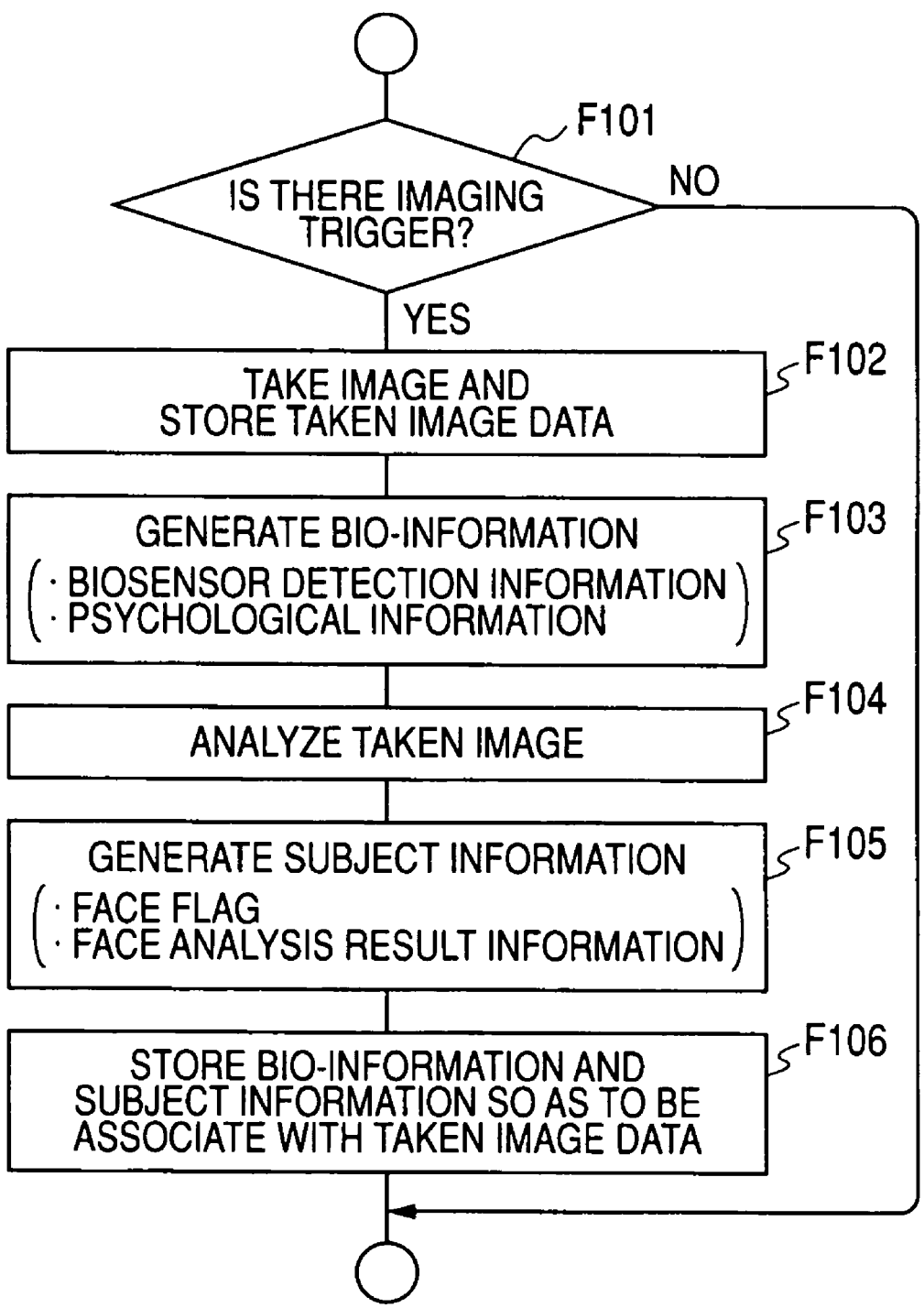

TAKEN IMAGE

TAKEN IMAGE

FIG. 6

| DATE AND TIME INFORMATION (YEAR, MONTH, DAY, HOUR, MINUTE, SECOND) | BIOSENSOR DETECTION INFORMATION | PSYCHOLOGICAL INFORMATION |

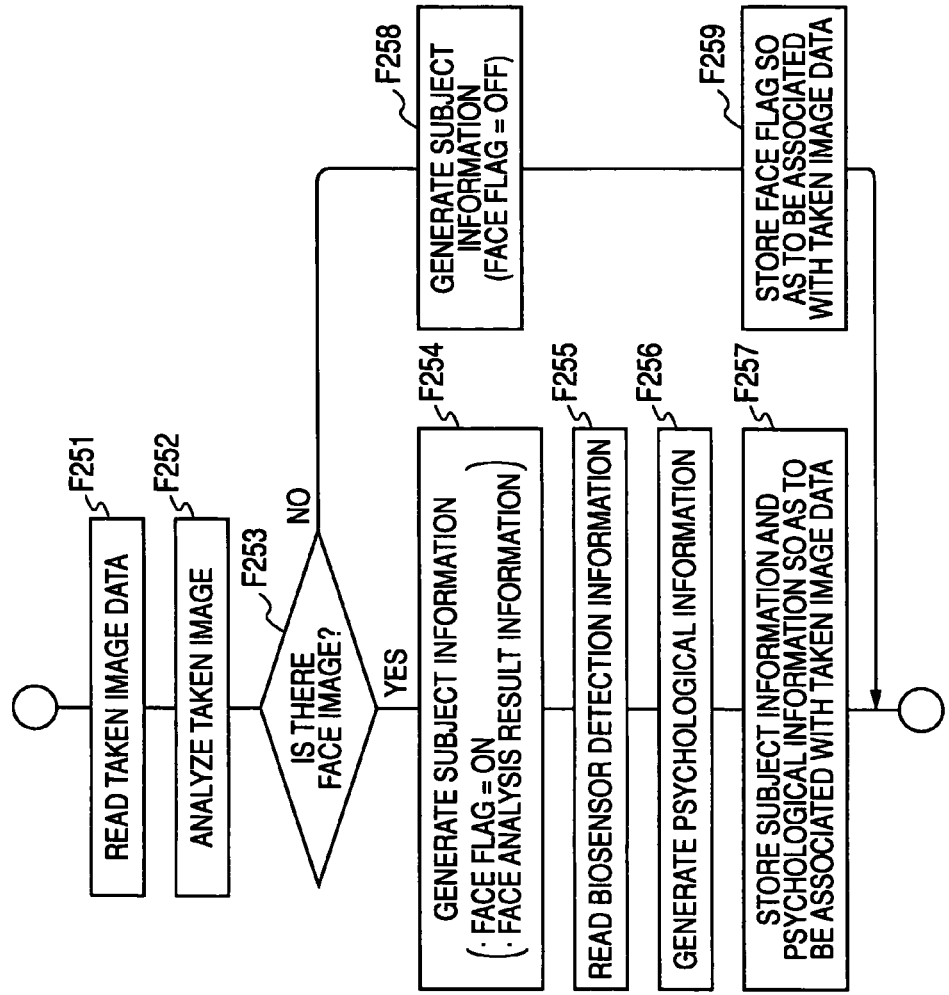
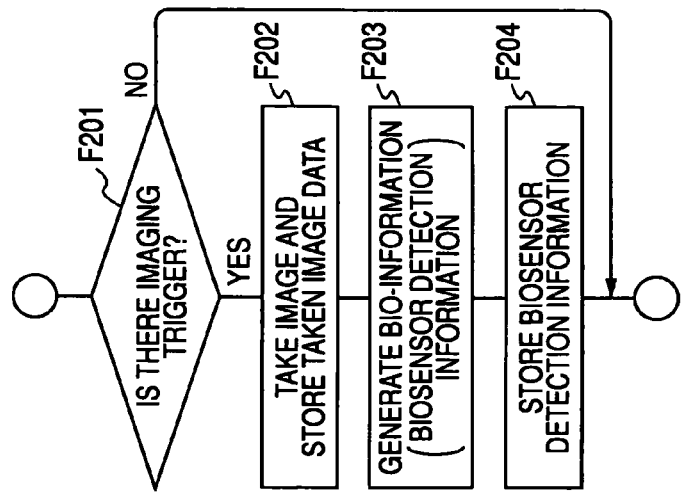
FIG. 7A
FIG. 7B

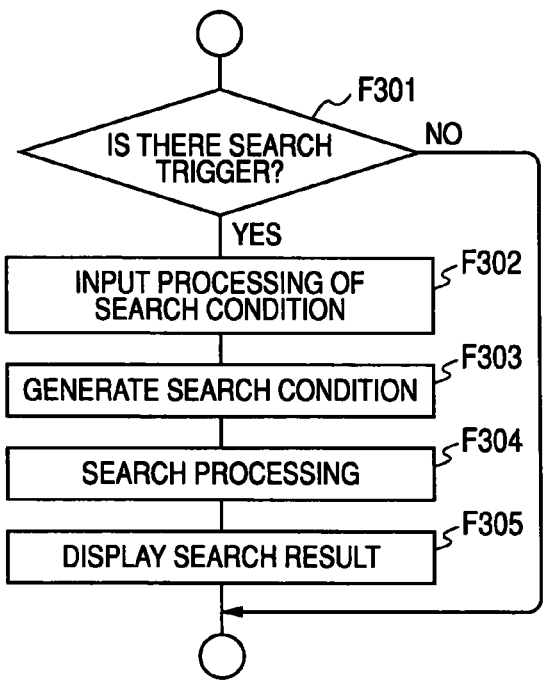
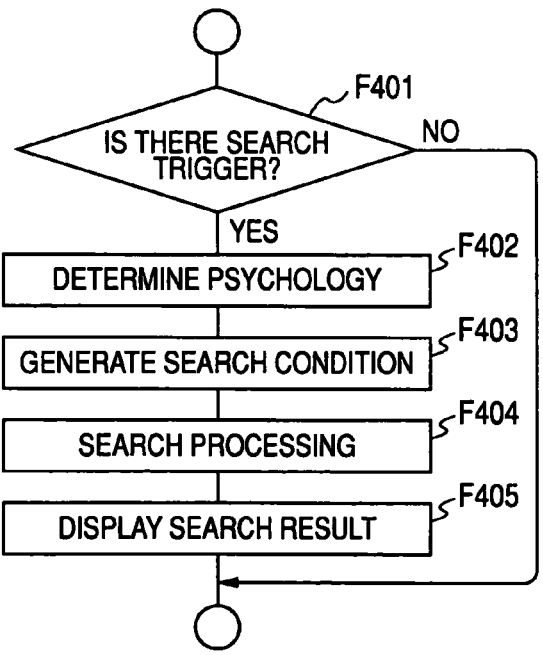

IMAGE STORAGE PROCESSING APPARATUS, IMAGE SEARCH APPARATUS, IMAGE STORAGE PROCESSING METHOD, IMAGE SEARCH METHOD AND PROGRAM

CROSS REFERENCE TO RELATED APPLICATIONS

The present invention contains subject matter related to Japanese Patent Application JP 2007-102659 filed in the Japanese Patent Office on Apr. 10, 2007, the entire contents of which being incorporated herein by reference.

BACKGROUND OF THE INVENTION

1. Field of the Invention

The invention relates to an image storage processing apparatus, an image search apparatus, an image storage processing method, an image search method for taken image data and a program realizing the above by an information processing apparatus.

2. Description of the Related Art

In JP-A-2005-260892 (Patent Document 1), a technology is disclosed, in which an image is recorded, taking an emotional up/down amplification signal by a heart electric signal as a trigger.

In JP-A-2005-250977 (Patent Document 2), a technology is disclosed, in which emotions (happy, sad, pleasant, angry, scared, cold, hot, comfortable, painful, depressed, etc.) of a person who takes images are reflected on taken images.

In JP-A-2004-178593 (Patent Document 3), a technology is shown, in which emotional information of a person who takes images is acquired, then, importance or the emotional information is analyzed based on the degree of interest, importance, the degree of taste to tag images, and particularly, analysis of face images of the person who takes image is described.

In JP-A-2005-124909 (Patent Document 4), a technology in which bio-information or psychology of a human being is put on still images or moving images is disclosed. A technology in which content search is performed by using bio-information is also described.

In JP-A-2005-141281 (Patent Document 5), a technology is enclosed, in which psychology and bio-information which are difficult to be expressed by text and the like are sensed to be added on contents to reproduce experiences, which are used for the search.

SUMMARY OF THE INVENTION

In recent years, there are circumstances where a user possesses a great deal of taken images due to the popularization of digital still cameras or video cameras. It is also assumable that images of user's action history of daily life are stored by continuously taking images (taking full-time continuous moving images, regularly taking still pictures and the like) in a state that the user carries a camera as a life slice camera. In this case, the user will possess further much taken image data. Under such circumstances, it is important to select and output (for example, display output) taken images from a great deal of taken image data easily and suitably.

It is desirable to provide a technical method of storing taken image data and performing searching for outputting the data.

According to an embodiment of the invention, an image storage processing apparatus includes an image acquisition means for acquiring taken image data imaged at an imaging apparatus unit, a bio-information acquisition means for acquiring bio-information of a user of the imaging apparatus unit at the time of imaging the taken image data acquired by the image acquisition means, a subject information acquisition means for acquiring subject information as an image analysis result of the taken image data acquired by the image acquisition means, and a storage processing means for performing processing of recording the taken image data acquired by the image acquisition means, the bio-information acquired by the bio-information acquisition means and the subject information acquired by the subject information acquisition means in a recording medium in a state in which the they are associated with one another.

The image acquisition means acquires taken image data by an imaging operation in the imaging apparatus unit which is integrally provided.

Alternatively, the image acquisition means acquires taken image data by an imaging operation in the external imaging apparatus unit.

The bio-information acquisition means acquires biosensor detection information as the bio-information.

The bio-information acquisition means generates psychological information of a user of the imaging apparatus unit as the bio-information by using biosensor detection information.

The subject information acquisition means performs image analysis of whether a face image of a person is included in taken image data or not, regarding face presence information which is an image analysis result as the subject information.

The subject information acquisition means performs image analysis of a face image of a person in taken image data, regarding face analysis result information which is the image analysis result as the subject information. The face analysis result information is information indicating, for example, expression, gender, an age bracket and the like.

Additionally, there are provided a search processing means for generating search conditions by using the bio-information and the subject information and performing search processing based on the search conditions with respect to taken image data stored so as to be associated with the bio-information and the subject information by the storage processing means, and an output processing means for performing output processing of a search processing result by the search processing means.

The search processing means further uses bio-information for generating search conditions, which is acquired by the bio-information acquisition means when the search processing is performed.

An image search apparatus according to an embodiment of the invention includes a search processing means for generating search conditions by using bio-information and subject information and performing search processing based on the search conditions as search processing with respect to a recording medium in which taken image data, the bio-information at the time of imaging by a user of an imaging apparatus unit imaged the taken image data and the subject information as an image analysis result of the taken image data are stored so as to be associated with one another, and an output processing means for performing output processing of a search processing result by the search processing means.

Additionally, a bio-information acquisition means for acquiring bio-information of a user is further included, and the search processing means further uses bio-information for generating search conditions, which is acquired by the bio-information acquisition means when the search processing is performed.

An image storage processing method according to an embodiment of the invention includes an image acquisition step of acquiring taken image data imaged at an imaging apparatus unit, a bio-information acquisition step of acquiring bio-information of a user of the imaging apparatus unit at the time of imaging taken image data acquired in the image acquisition step, a subject information acquisition step of acquiring subject information as an image analysis result of taken image data acquired in the image acquisition step and a storage processing step performing processing of recording the taken image data acquired in the image acquisition step, the bio-information acquired in the bio-information acquisition step and the subject information acquired in the subject information acquisition step in a recording medium in a state in which they are associated with one another.

A program according to an embodiment of the invention is a program allowing an information processing apparatus to execute the image storage processing method.

An image search method according to an embodiment of the invention includes a search processing step of generating search conditions by using bio-information and subject information and performing search processing based on the search conditions as search processing with respect to a recording medium in which taken image data, the bio-information at the time of imaging by a user of an imaging apparatus unit imaged the taken image data and the subject information as an image analysis result of the taken image data are stored so as to be associated with one another, and an output processing step of performing output processing of a search processing result by the search processing step.

A program according to an embodiment of the invention is a program allowing an information processing apparatus to execute the image search method.

That is to say, in the embodiments of the invention, bio-information of a user at the time of imaging and subject information in a taken image are stored in a state in which the information is associated to taken image data.

At the time of searching, search conditions are generated by using the bio-information and the subject information to perform searching. Bio-information at the time of searching is also used for generating search conditions.

The subject information in the taken image is for example, information concerning an image of a person taken in the taken image. Accordingly, an image suitable for the user can be selected and displayed by taking emotions and the like of a person who takes the image and an expression and the like of a person as the subject as conditions, further, by adding emotions and the like of a user at the time of searching.

According to the embodiments of the invention, the bio-information of a user at the time of imaging and subject information in a taken image are stored in a state in which the information is associated with taken image data, thereby performing searching by using the bio-information and the subject information at the time of searching. Additionally, it is possible to perform searching in which bio-information (emotions and the like) of a user at the time of searching is added. Accordingly, there is an advantage that image selection and display suitable to a viewer of images can be realized.

Particularly, search conditions are properly set by adding psychology of a viewer, thereby calming or control the mind of the viewer.

BRIEF DESCRIPTION OF THE DRAWINGS

FIG. 2 is a block diagram of the imaging apparatus according to an embodiment;

FIG. 3 is a flowchart of an image storage processing example I according to an embodiment;

FIG. 6 is an explanatory diagram of a storing state of bio-information according to an embodiment;

FIG. 7A and FIG. 7B are flowcharts of an image storage processing example II according to an embodiment;

FIG. 8 is a flowchart of an image search processing example I according to an embodiment;

FIG. 9 is a flowchart of an image search processing example II according to an embodiment;

DESCRIPTION OF THE PREFERRED EMBODIMENTS

Hereinafter, an image storage processing apparatus, an image search apparatus, an image storage processing method and an image search method and a program according to embodiments of the invention will be explained.

In this case, an imaging apparatus is cited as an example of an apparatus in which an image storage processing apparatus and an image search apparatus are combined. The image storage processing apparatus and the image search apparatus according to an embodiment of the invention can be realized in apparatuses other than the imaging apparatus, which will be described as modification examples and extension examples.

The explanation will be made in the following order.
[1. Appearance examples of an imaging apparatus]
[2. Configuration example of the imaging apparatus]
[3. Image storing processing example I]
[4. Image storing processing example II]
[5. Image search processing example I]
[6. Image search processing example II]
[7. Advantage of the embodiments, modification examples, extension examples and programs]
[1. Appearance Examples of an Imaging Apparatus]

Various forms can be considered as an imaging apparatus 1 of an embodiment, and appearance examples thereof will be cited as examples in FIG. 1A, FIG. 1B, FIG. 1C and FIG. 1D.

Figure 1A:
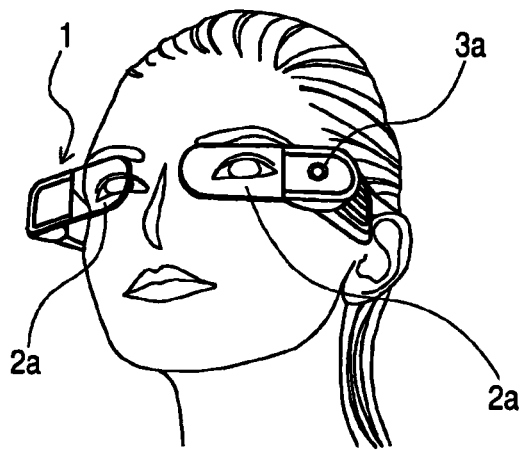
FIG. 1A to FIG. 1D are explanatory views of appearance examples of an imaging apparatus according to an embodiment of the invention.

FIG. 1A shows an imaging apparatus 1 as a glasses-type display camera. The imaging apparatus 1 includes a wearable unlit having a configuration in which, for example, a frame goes half around from both temporal regions to an occipital region, which is worn by the user, being hung on the user's both auricles as shown in the drawing.

In the imaging apparatus 1, an imaging lens 3a is arranged, facing forward, so as to take images of the direction of user's sight as the subject direction in a state of being worn by the user.

In the wearing state as shown in the drawing, the imaging apparatus 1 has a configuration in which a pair of display panel units 2a, 2a for right and left eyes is arranged at positions just before both eyes of the user, namely, where lenses in the normal glasses are located. For the display panel unit 2a, for example, a liquid crystal panel is used, which can be in a see-through state, namely, a transparent or a semitransparent state by controlling the transmittance. As the display panel unit 2a is in the see-through state, the user does not have any trouble in daily life even if the user constantly wears the apparatus like glasses.

As the display panel unit 2a, in addition to the configuration in which a pair of units are provided so as to correspond to both eyes, a configuration in which one unit is provided so as to correspond to one eye.

Figure 1B:
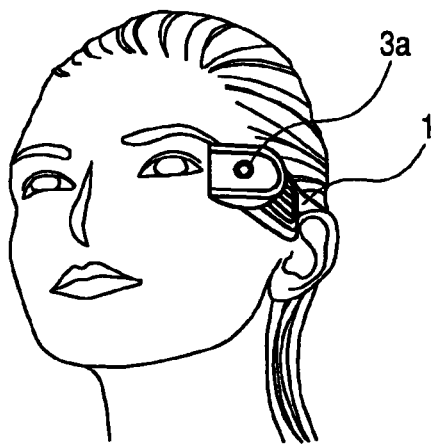

FIG. 1B also shows an imaging apparatus 1 to be worn by the user at the head, having a configuration in which the display panel unit 2a as shown in FIG. 1A is not included. The apparatus is worn at the user's head by a wearing unit, for example, which can be hung at an auricle. In this state, an imaging lens 3a is arranged, facing forward, so as to take images of the direction of user's sight as the subject direction in this state.

In FIG. 1A and FIG. 1B, the imaging apparatuses 1 which are worn at the user's head by the glasses-type wearing unit or the wearing unit to be worn at the head are cited, however, the configuration whereby the user wears the imaging apparatus 1 can be variously considered. The imaging apparatus 1 can be worn by the user by any type of wearing units such as a headphone type, a neckband type, and an ear-hang type. In addition, the imaging apparatus 1 may have a configuration in which the user wears the apparatus by being attached to normal glasses, a visor, headphones and the like by attachments such as a clip. Furthermore, the apparatus does not always have to be worn at the user's head.

Though the imaging direction was the direction of user's sight in the above, a configuration in which the imaging lens 3a is attached so as to take images of backward, lateral, upper and lower directions when the user wears the apparatus or a configuration in which plural imaging systems whose imaging directions are the same or different directions are provided can be considered.

Moreover, in one or plural imaging lenses 3a, imaging direction variable mechanism which can vary the subject direction manually or automatically can be provided.

Figure 1C:
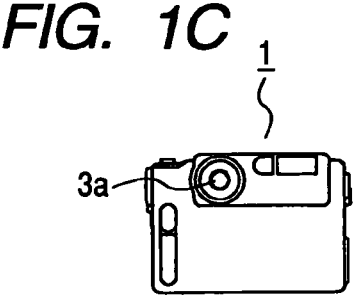

FIG. 1C shows an imaging apparatus 1 in a form generally known as a digital still camera.

Figure 1D:
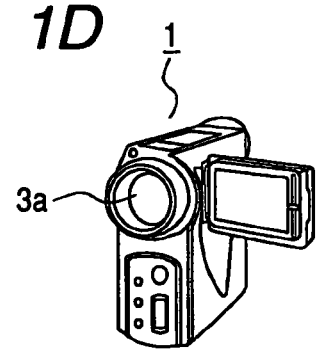

FIG. 1D shows an imaging apparatus 1 in a form generally known as a video camera.

The imaging apparatuses 1 possessed and used by the user as shown in FIG. 1C and FIG. 1D can be embodiments of the invention. In the drawings, only the imaging lens 3a is shown, however, a panel display unit for imaging monitor and a display device such as a viewfinder are also provided.

It goes without saying that other forms other than the forms shown in FIG. 1A, FIG. 1B, FIG. 1C and FIG. 1D can be considered as an imaging apparatus taking still images and moving images. For example, apparatuses such as a cellular phone device, a PDA (Personal Digital Assistant), and a portable personal computer which include the function as the imaging apparatus can be considered as the imaging apparatus 1 of the embodiment.

In these various forms, it is also preferable that, for example, a microphone collecting external audio is provided and audio signals to be recorded with image data are obtained at the time of taking images. Furthermore, it is preferable that a speaker unit or an earphone unit outputting audio is formed.

It can be considered that a light emitting unit illuminating the subject direction is provided by a LED (Light Emitting Diode) in the vicinity of the imaging lens 3a, or that a flash light emitting unit for taking still images is provided.

In the imaging apparatus 1 of the embodiment, one of or both of a manual imaging and an automatic imaging can be executed as imaging operations.

In this case, the "manual imaging" indicates an operation in which imaging is performed (taken image data is recorded) by shutter operations by the user.

On the other hand, the "automatic imaging" indicates an operation in which imaging is performed (taken image data is recorded) not by shutter operations by the user. For example, when the imaging apparatuses 1 shown in FIG. 1A and FIG. 1B are worn by the user, an operation of continuously taking moving images or an operation of taking still images at intervals of one second, several seconds, several dozen seconds are considered as the automatic imaging operations. For example, the operation of taking images of user's history of daily life as a life slice camera. The operation of performing imaging by some kinds of triggers other than the user operation, though not a regular imaging operation, can be considered as the automatic imaging operation. For example, the operation in which the imaging is automatically performed by detecting user's emotions such as tension or amazement, and the operation in which imaging is performed by triggers supplied from an outer apparatus (triggers other than user's shutter operation information) are considered as the automatic imaging operation.

[2. Configuration Example of the Imaging Apparatus]

A configuration example of the imaging apparatus 1 will be explained with reference to FIG. 2.

A system controller 10 includes a microcomputer which has, for example, a CPU (Central Processing Unit), a ROM (Read Only Memory), a RAM (Random Access Memory), a nonvolatile memory unit and an interface unit, which forms a control unit controlling the whole imaging apparatus 1. The system controller 10 performs various calculation processing and gives and receives control signals and the like to and from respective units through a bus 13 based on programs stored in the internal ROM and the like, allowing the respective units to execute necessary operations.

An imaging unit 3 includes an imaging optical system, an imaging device unit and an imaging signal processing unit.

The imaging optical system in the imaging unit 3 is provided with a lens system including an imaging lens 3a shown in FIGS. 1A to 1D, a diaphragm, a zoom lens, a focus lens and the like, a drive system for allowing the lens system to perform focusing operation or a zooming operation, and the like.

The imaging device unit in the imaging unit 3 is provided with a solid-state imaging device array detecting imaging light obtained by the imaging optical system and generating imaging signals by performing photoelectric conversion. As the solid-state imaging device array, for example, a CCD (Charge Coupled Device) sensor array, or a CMOS (Complementary Metal Oxide Semiconductor) sensor array is used.

The imaging signal processing unit in the imaging unit 3 includes a sample-and-hold/AGC (Automatic Gain Control) circuit performing gain adjustment and waveform shaping with respect to signals obtained by the solid-state imaging devices and a video A/D converter acquiring taken image data as digital data. The imaging signal processing unit performs white balance processing, luminance processing, color signal processing, a blur correction processing and the like with respect to the taken image data.

The imaging is performed by the imaging unit 3 including the imaging optical system, the imaging device unit and the imaging signal processing unit to obtain taken image data.

The image data obtained by the imaging operation by the imaging unit 3 is processed in an imaging control unit 6.

The imaging control unit 6 performs processing of converting the taken image data into a given image data format or a processing of supplying the converted taken image data to a subject information generating unit 12, a storage unit 14, a communication unit 15 and a display control unit 7 according to an operation status under control of the system controller 10.

The imaging control unit 6 also performs on/off control of imaging operation in the imaging unit 3, drive control of the zoom lens and focus lens of the imaging optical system, control of sensitivity of the imaging device unit or a frame rate, parameter control or setting of execution processing of various processing in the imaging signal processing unit based on instructions of the system controller 10.

The subject information generating unit 12 performs image analysis processing with respect to taken image data obtained by the imaging apparatus 1, that is, the taken image data taken by the imaging unit 3 to generate subject information.

Particularly, as the image analysis processing, analysis processing analyzing whether a human face is included in a taken image or not is performed. The subject information generating unit 12 generates a face flag as information indicating the presence of a face image (face presence information) according to the presence/absence of the face image.

For example, whether there is a face image in the image in taken image data or not can be determined by recognizing components of a face such as eyes, a nose, a mouth and an outline of the face in the image.

In the case that there is a face image, the subject information generating unit 12 further performs analysis processing of the face image, generating face analysis result information also as subject information. The face analysis result information is information indicating, for example, expression, gender or an age bracket of a person whose image is taken.

It is known that expression, gender and the age bracket can be estimated by the analysis of the face image at a certain degree of probability.

The processing of determining face expression can be variously considered. For example, a method of determining expression by extracting parts forming the face and giving evaluation values to respective parts to determine expression can be applied.

For example, in the case of determining a smiling face, respective parts of eyes, eyebrows, lips are extracted from the image as parts forming the face. Concerning the eyebrows, an angle is determined. A low point is given to a so-called "slanting up" state and a higher point is given to eyebrows whose both ends slant down. Concerning the eyes, the dilation degree of pupils is determined. A higher point is given to eyes whose pupils are widely dilated. Concerning lips, a lower point is given to lips whose angles of both ends slant down, whereas, a higher point is given to lips whose angles of both ends slant up.

As described above, for example, points for determining a smiling face are given to respective parts, adding these points (or performing additions by changing weights according to parts) to calculate a smiling face point. When the smiling face point is higher than a predetermined value, the smiling face can be determined.

Needless to say, this is just an example, and it is also preferable that a state of cheeks, wrinkles generated when a person smiles and the like can be used as determination factors.

It is also possible to estimate expressions other than the smiling face, such as an angry expression, a bad-tempered expression, a sad expression, a calm expression from the image of respective parts forming the face.

A biosensor 4 includes various sensors detecting various kinds of bio-information of the user. For example, a blood-pressure sensor, a body-temperature sensor, a pulse sensor, a brain-wave sensor, an electric reaction sensor, a skin-resistance value sensor, a visual sensor, and other various kinds of sensors can be considered. An acceleration sensor, an angular velocity sensor, a vibration sensor and the like can be also considered.

The bio-information generating unit 5 acquires bio-information as detected information by various sensors of the biosensor unit 4.

Information detected by various sensors of the biosensor unit 4 (biosensor detection information) indicates, for example, a pulse rate, a heart rate, electrocardiographic information, myoelectric information, breathing information (such as speed, depth, ventilation amount of breathing), perspiration, GSR (galvanic skin response), blood pressure, oxygen saturated level in the blood, skin surface temperature, brainwaves (information of $\alpha$ waves, $\beta$ waves, $\theta$ waves and $\delta$ waves), bloodstream change, eye condition and the like.

As the detection information by the acceleration sensor, the angular velocity sensor and the vibration sensor, information of acceleration, angular velocity and vibration can be regarded as bio-information indicating motions of the user.

The bio-information generating unit 5 can also determine user's psychological status based on the biosensor detection information and generates psychological information as one of the bio-information.

For example, it is possible to estimate user's emotions (joyful, interesting, happy, sad, scared, calm, nostalgic, touching, amazing, exiting, tense and the like) based on variations of numeric values of the biosensor detection information detected from a state of tension, an excited state, a comfortable state and the like. Moreover, user's status can be determined by the state of pupils, visual line motions by the visual sensor. It is also preferable that motions of user's body detected by the acceleration sensor, the vibration sensor and the like are used for the determination of user's status.

The cause of increasing of the frequency of the pulse and the like is sometimes tension or excitement, or sometimes user's exercise such as running. It is also preferable that the cause is determined by referring information of the acceleration sensor and the like.

That is, it is possible to estimate user's emotional state by using one or plural detection information by various sensors. The bio-information generating unit 5 can generate psychological information by performing the described estimation processing.

A certain degree of time is necessary for estimating the psychological state, and it is sometimes difficult to estimate an accurate psychological state only by temporarily taking detection information of the biosensor unit 4. That is, the value of detection information by the biosensor unit 4 as a signal obtained from a body constantly changes, therefore, it is difficult to determine the psychological state only by referring a value of a certain moment. There are some cases in which a threshold for determining the psychological state should be changed by consecutive changes of emotions.

It is preferable that the bio-information generating unit 5 constantly takes bio-information in the biosensor unit 4 without stopping and generates psychological information of the user by adding changes of the time-series detection information.

The various sensors in the biosensor unit 4 may touch the temporal regions or the occipital region of the user by being arranged inside the wearing frame of the glasses-type imaging apparatus 1 to detect the various information, and it is also preferable that they are worn at given positions in the body, separated from the wearing frame portion of the imaging apparatus 1. For example, it is preferable that the sensor touches a wrist of the user and the like by a watch-shaped unit and the like. For detecting the state or motions of eyes, the state of pupils and the like, it can be considered that a camera taking images of user's eye is used.

The subject information generating unit 12 or the bio-information generating unit 5 can be configured by a microcomputer or a DSP (Digital Signal Processor) as a video processor. Though the subject information generating unit 12 and the bio-information generating unit 5 are shown by different blocks from the system controller 10 including the microcomputer in FIG. 2, it is also preferable that operations as the subject information generating unit 12 or the bio-information generating unit 5 are realized by software activated in the system controller 10.

As configurations performing display for the user in the imaging apparatus 1, a display unit 2 and a display control unit 7 are provided.

The display unit 2 is provided with the display panel unit 2a including the above-described liquid crystal panel and the like and a display drive unit driving the display of the display panel unit 2a.

The display drive unit includes a pixel drive circuit for displaying image data supplied from the imaging control unit 6 on the display panel unit 2a which is, for example, a liquid crystal display. The pixel drive circuit applies drive signals based on video signals at the respective prescribed horizontal/vertical driving timing to respective pixels arranged in a matrix state in the display panel unit 2a to perform the display.

The display control unit 7 drives the pixel drive circuit in the display unit 2 and performs a given display on the display panel unit 2a under control of the system controller 10.

That is, the display control unit 7 executes the display as the imaging monitor in the imaging unit 3, the playback display of taken image data taken by the storage unit 14, the display of data received by the communication unit 15, the display of various characters and the like on the display panel unit 2a.

For the above displays, for example, luminance level adjustment, color correction, contrast adjustment, sharpness (outline emphasis) adjustment and the like can be performed. In addition, image effect processing such as generation of an enlarged image in which part of image data is enlarged or generation of a shrunk image, soft focusing, mosaic, luminance inversion, highlight display (emphatic display)- of part of the image, and the change of the whole color atmosphere, separation and composition of images for divided display of taken images, generation of character images or imagery images and processing of combining a generated image with a taken image and the like can be performed.

The display control unit 7 controls display drive unit based on instructions by the system controller 10, controlling transmittance of respective pixels in the display panel unit 2a so as to be the see-through state (transparent or semitransparent state).

The storage unit 14 is used for storing various kinds of data. For example, it is used for storing taken image data. The storage unit 14 also stores bio-information (biosensor detection information and psychological information) generated in the bio-information generating unit 5, or stores subject information (face flags and face analysis result information) generated in the subject information generation unit 12, associating these information with the taken image data.

The storage unit 14 may be configured by a solid-state memory such as a RAM or a flash memory or, may be configured by, for example, a HDD (Hard Disk Drive).

It is also preferable that the storage unit 14 may be a recording/playback drive, not internal recording media, which corresponds to portable recording media such as a memory card including a solid-state memory, an optical disc, an magnetic optical disc, and a hologram memory.

Needless to say, both the internal memory such as the solid-state memory or the HDD and the recording/playback drive corresponding to the portable recording media can be mounted.

The storage unit 14 records taken image data, bio-information, subject information and the like and stores them under control of the system controller 10.

The storage unit 14 reads the recorded data and supplies it to the system controller 10, the display control unit 7 and the like under control of the system controller 10.

The communication unit 15 transmits and receives data to and from external apparatuses. The communication unit 15 may have a configuration in which network communication is performed through, for example, a near-field wireless communication with respect to a network access point in the wireless LAN, the Bluetooth standard and the like, and the communication unit 15 may also perform wireless communication directly between external apparatuses having corresponding communication functions.

It is not always have to be wireless communication but also preferable that the communication unit 15 performs communication with external apparatuses through cable connection.

In the imaging apparatus 1, an operation input unit 11 is provided for operations by the user. Operation inputs for an operation of on/off of power supply, a selection operation of automatic imaging/manual imaging, a shutter operation at the time of manual imaging (or operation of start/stop of recording moving images), an operation of zooming/focusing, an operation of designating display contents, a later-described operation of instructing search and the like are performed by the operation input unit 11.

The operation input unit 11 may have a configuration in which operation elements such as keys, dials are included and the user operation is detected as a key operation and the like, or a configuration in which user's conscious behavior is detected.

When the operation elements are provided, it is necessary to provide operation elements used for the operation of on/off of power supply, the operation of the imaging system (for example, operations of the shutter, zooming and the like, the instruction operation of signal processing), operations concerning the display (for example, selection of display contents or display adjustment operation) and so on.

It is also preferable to provide a touch pad or a touch panel as operation elements. For example, the touch panel is arranged in the display unit 2, and operation input is performed by the user, touching a display screen.

It is also preferable to provide the touch panel, a cross key, a jog dial and the like as operation elements for moving a pointer such as a cursor on the screen. It is possible to allow the operation of moving the cursor and the like on the screen by a remote controller including an acceleration sensor, an angular velocity sensor and the like operated by the user who holds and moves the remote controller.

The operation input unit 11 supplies operation information inputted by the above operations to the system controller 10, and the system controller 10 performs designated control according to the operation information.

In the case of including the biosensor unit 4 as described above, it can be considered that the system controller 10 detects the conscious operation input by the user based on the detection information by the biosensor unit 4.

For example, a knock from a side surface of the imaging apparatus 1 by the user is detected by the acceleration sensor, the vibration sensor and the like, and when the acceleration in the lateral direction exceeds a fixed value, the system controller 10 recognizes the knock as the user's operation. In this case, when the accelerator sensor or the angular velocity sensor can detect which of side parts (parts which corresponds to bows of glasses) has been knocked by the user, namely, at the right side or at the left side, it is possible to determine the detected results as respective prescribed operations.

It is also possible that the acceleration sensor or the angular velocity-sensor detects user's motions like turning the head, or shaking the head and the system controller 10 recognizes the detected motion as the user's operation.

It can be also considered that a pressure sensor is arranged at the right-and-left side parts (parts corresponding to bows of glasses) and the like of the imaging apparatus 1, and that the operation of pushing the right side by the user's finger is recognized as a zooming operation in the long-distance direction, and the operation of pushing the left side by the user's finger is recognized as a zooming operation in the wide-angle direction.

As the conscious behavior of the user, for example, motions of eyes (variation of visual line directions and blinks) can be considered. It is possible, when the visual sensor detects three blinks of the user, to determine the operation as a particular operation input. Moreover, according to the detection information of the biosensor unit 4, motions of user's wearing and removing the imaging apparatus 1, or a motion of a particular user who wears the imaging apparatus 1 can be detected, and it is preferable that the system controller 10 performs on/off of power supply according to the detection.

Configurations in which the operation input is detected by other sensors such as a sensor of detecting user's voice, a sensor detecting motions of lips can be considered.

The configuration of the imaging apparatus 1 has been described above, however, it is just one example. Depending on operational examples or functions performed in actual, addition and deletion of various components can be naturally considered.

[3. Image Storing Processing Example I]

Storing processing of taken image data performed in the imaging apparatus 1 will be explained. FIG. 3 shows processing performed in the system controller 10, the bio-information generating unit 5 and the subject information generating unit 12. When the bio-information generating unit 5 and the subject information generating unit 12 are formed by software operating in the microcomputer which is the system controller 10, the processing of FIG. 3 can be considered as the processing of the system controller 10. This is the same in FIGS. 7A and 7B which will be described later.

The system controller 10 checks an occurrence of an imaging trigger in Step F101. The system controller 10 recognizes some signal as the occurrence of the imaging trigger to perform imaging in the imaging apparatus 1.

In the case of performing the manual imaging, the shutter operation using the operation input unit 11 by the user or the shutter operation by the user's conscious behavior detected by the biosensor unit 4 is recognized as the imaging trigger.

In the case of performing the automatic imaging, the following imaging triggers can be considered.

For example, in the case of performing constantly continuous imaging when the user wears the imaging apparatus 1 shown in FIG. 1A or FIG. 1B, if the user's wearing is detected by detection information by the biosensor unit 4, it can be considered as the occurrence of the imaging trigger. The operation of turning on power supply can be considered as the occurrence of the imaging trigger.

In the case of taking still images regularly, the system controller 10 determines the occurrence of the imaging trigger every time a fixed period of time has passed according to the count of an internal timer.

The automatic imaging performing imaging automatically can be performed, for example, when the user is excited/frantic when watching sports, when the user witnesses an interesting scene, when the user is moved, when the user witnesses a traffic accident and the like, when the user encounters a favorite person/celebrity, when the user feels anxiety or fear, when the user is surprised. For example, the bio-information generating unit 5 constantly monitors detection information of the biosensor unit 4, estimating the user's psychological status constantly, and when the psychological statuses such as amazing, exciting, joyful, anxious and the like are estimated, the estimation may be notified to the system controller 10 as the imaging trigger.

The system controller 10, when recognizing the imaging trigger, allows the process to proceed from Step F101 to Step F102, performing control of executing imaging and storing of taken image data. Hereinafter, explanation will be made in a condition that still images are taken as the imaging operation.

The system controller 10 instructs the imaging control unit 6 to take images and to take taken image data obtained in the imaging unit 3, namely, taken image data of one frame at the timing prescribed by the imaging trigger. The system controller 10 also instructs transfer of the taken image data to the storage unit 14 and instructs the storage unit 14 to store the data in a recording medium.

Next, the system controller 10 instructs the bio-information generating unit 5 to generate bio-information in Step F103. The bio-information generating unit 5 regards detected values (biosensor detection information) of respective sensors of the biosensor unit 4 at the imaging timing as bio-information.

The psychological information of the user detected at this point is also regarded as bio-information.

As described above, it is more preferable that the user's psychological status is estimated by continuously monitoring biosensor detection information and considering the variation of the information rather than it is estimated from biosensor detection information at a certain moment. Therefore, the bio-information generating unit 5 constantly monitors biosensor detection information and continues the processing of estimating the psychological status. In the Step F103, it is preferable that the psychological status estimated at that time is outputted as psychological information at the time of imaging.

The system controller 10 instructs the subject information generating unit 12 to analyze taken image data in Step S104. Then, the system controller 10 instructs the subject information generating unit 12 to generate subject information in Step F105.

That is to say, the system controller 10 transfers the taken image data from the imaging control unit 6 also to the subject information generating unit 12. The subject information generating unit 12 performs analysis of the transferred taken image data according to the instruction of the system controller 10. First, the analysis whether there is a face image in the image or not is performed.

Figure 4A:
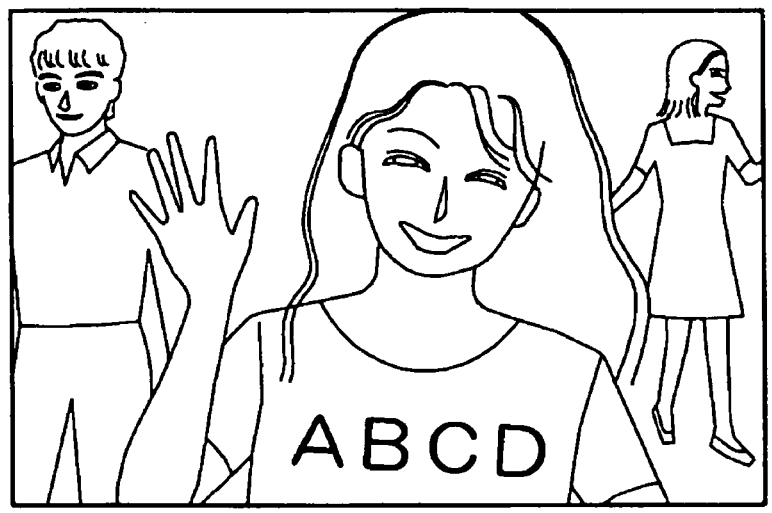
FIG. 4A and FIG. 4B are explanatory views of taken images including face images according to an embodiment.
Figure 4B:
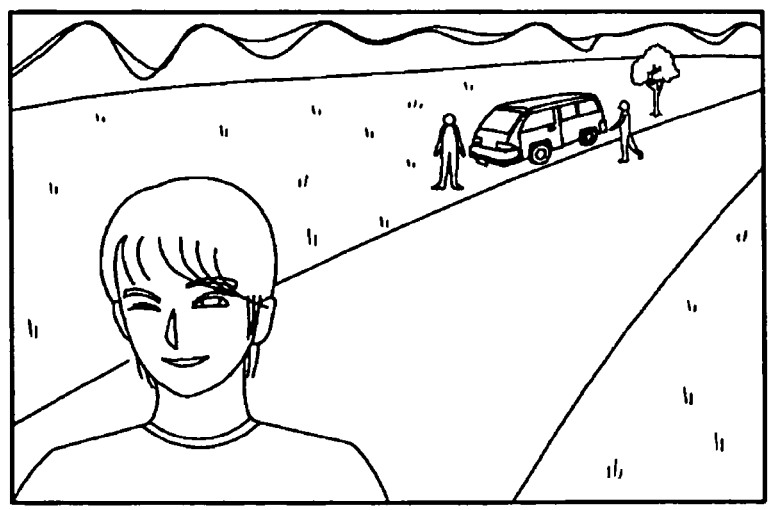

For example, when the taken image data has image contents as shown in FIG. 4A or FIG. 4B, the presence of face image is confirmed.

When there is a face image, the subject information generating unit 12 analyzes the face image and performs estimation processing such as expression, gender and the age bracket.

The subject information generating unit 12 generates subject information based on the analysis result. When there is not a face image in the image of the taken image data, the subject information generating unit 12 generates information indicating that the face flag is off as subject information.

On the other hand, when there is a face image in the image of the taken image data and the analysis of the face image has been done, the subject information generating unit 12 generates information indicating the face flag is on, and generates face analysis result information as subject information. The face analysis result information is estimated information of expression, gender and the age bracket.

When the presence of plural face images are confirmed as in FIG. 4A, it is preferable to perform face-analysis with respect to all face images and generate face analysis result information with respect to the plural face images respectively, however, it is also preferable, for example, that a major face image is estimated and the analysis of that face image is performed to obtain face analysis result information. The major face image may be determined as the greatest face image in the size of the face image (the number of pixels occupied by the face image, the length of a diagonal line of the face image and the like) in the image, or to be the face image positioned at the center in the screen as compared with the other face images.

When a small face image is recognized in the distance as in FIG. 4B, it is preferable that the small face image is not recognized as the face image. That is, it is preferable to perform analysis processing so as to ignore face images smaller than a predetermined value.

Next, the system controller 10 stores bio-information and subject information in a state in which the information is associated with taken image data in Step F106. That is, bio-information generated in the bio-information generating unit 5 and subject information generated in the subject information generating unit 12 are supplied to the storage unit 14 and stored in the storage unit 14 in a state in which they are associated with the taken image data recorded in Step F102.

The above processing is performed when imaging is performed, as a result, taken image data, bio-information (bio-sensor detection information and psychological information), subject information (face flag and face analysis result information) are associated and stored in the storage unit 14.

Figure 5:
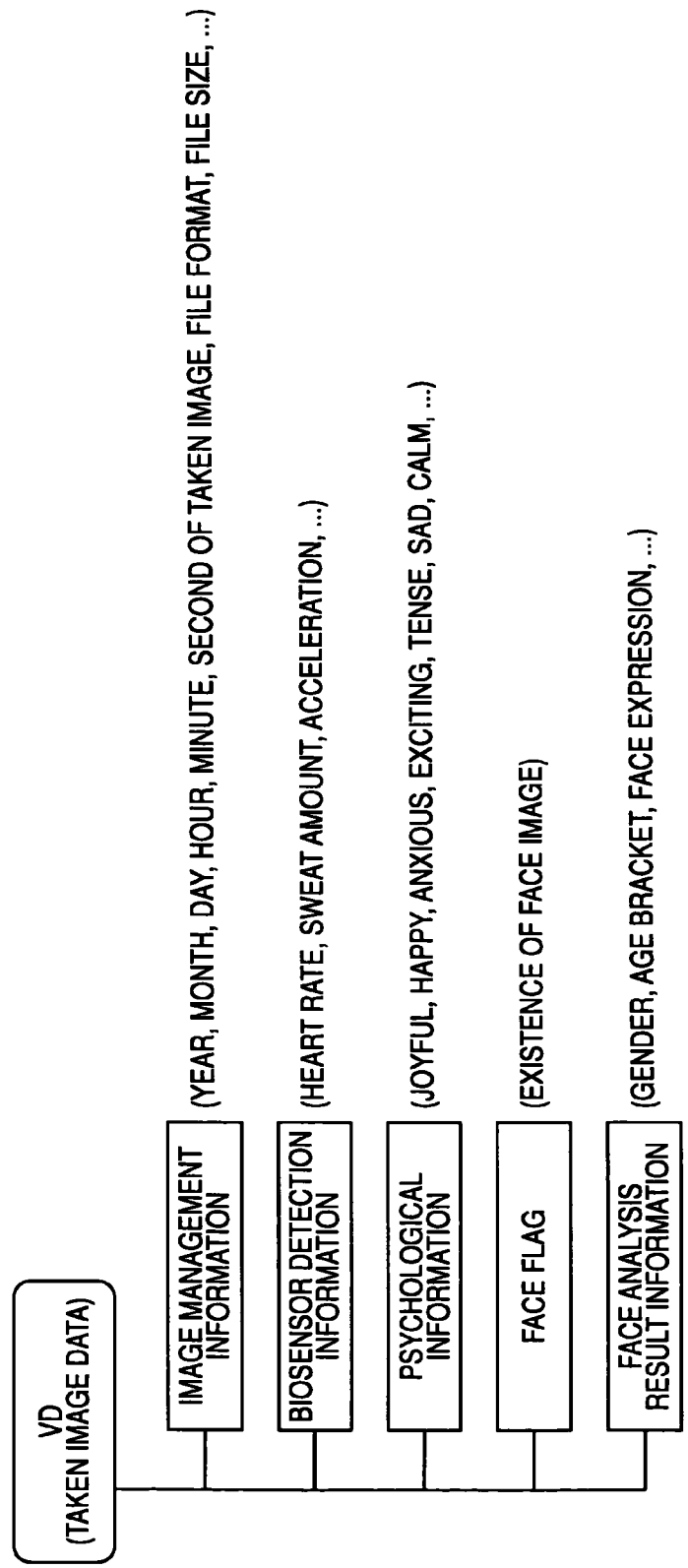
FIG. 5 is an explanatory diagram of a storing state of taken image data according to an embodiment.

For example, FIG. 5 shows an example of a storing state, indicating a state in which image management information, bio-sensor detection information, psychological information, face flag, and face analysis result information are stored with respect to one taken image data VD.

The image management information is information recorded together when the taken image data is recorded in Step S102. For example, information such as the imaging date (year, month, day, hour, minute, second), an image type, a file format, a compression format, and the data size is included.

The information is generated by the system controller 10 at the time of imaging and stored in the storage unit 14 with the taken image data VD.

As the biosensor detection information, a heart rate, a perspiration amount, a blood pressure value, body temperature, a galvanic skin response value, acceleration and the like as detected values of the biosensor unit 4 are recorded.

As psychological information, information of estimation results such as joyful, happy, anxious, exciting, tense, sad, calm is recorded.

As the face flag, information of flag-on/flag-off according to presence/absence of the face image is recorded.

As the face analysis result information, information of estimated results of gender, the age bracket and expression is recorded.

In the processing of FIG. 3, bio-information is generated and recorded with the taken image data VD at the time of imaging, and the biosensor detection information and the psychological information are recorded so as to be associated with the taken image data VD as in FIG. 5, however, it is also preferable that the bio-information is constantly recorded, separated from the imaging timing.

For example, the bio-information generating unit 5 generates bio-information as shown in FIG. 6 regularly. The bio-information is generated in a data format having biosensor detection information and psychological information with date and time information (year, month, day, hour, minute, second). The bio-information of FIG. 6 generated regularly is recorded in the storage unit 14.

When the bio-information is recorded with the date and time information as the above, it can be associated with the taken image data VD.

That is to say, concerning the taken image data VD recorded in the storage unit 14, corresponding (namely, at the time of imaging) bio-information can be discriminated based on date and time information in the image management information.

[4. Image Storing Processing Example II]

The above image storing processing example I of FIG. 3 is the example in which the biosensor detection information, the psychological information, the face flag, the face analysis result information corresponding the taken image data are generated and stored at the time of imaging. However, the generation and storing of the psychological information, the face flag and the face analysis result information is executed at the time other than the imaging time. In FIGS. 7A and 7B, an example of processing in which the generation and storing of the psychological information, the face flag and the face analysis result information are performed at the point of time later than the imaging time is shown as an image storing processing example II.

FIG. 7A shows the processing of the system controller 10 at the time of imaging.

The system controller 10, when recognizing an imaging trigger as described above, allows the process to proceed from Step F201 to F202, performing control of executing imaging and storing of the taken image data. That is, the system controller 10 instructs the imaging control unit 6 to take images and to execute taking of the taken image data obtained in the imaging unit 3, namely, the taking of the taken image data of one frame at the timing prescribed by the imaging trigger. The system controller 10 also transfers the taken image data to the storage unit 14 and instructs the storage unit 14 to store the data in a recording medium.

Next, the system controller 10 instructs the bio-information generating unit 5 to generate bio-information in Step F203. In this case, the bio-information generating unit 5 regards detected values of respective sensors of the biosensor unit 4 (biosensor detection information) at this imaging timing as bio-information.

Then, the system controller 10 stores the bio-information (only the biosensor detection information in this case) so as to be associated with the taken image data in Step F204. That is, the biosensor detection information generated in the bio-information generating unit 5 is supplied to the storage unit 14, and the information is recorded in a state in which the information is associated with the taken image data recorded in Step F202 in the storage unit 14.

In this case, it is preferable that detected values including time-series variations in a certain period of time until reaching the imaging timing are applied as the biosensor detection information.

The system controller 10 performs processing of FIG. 7B after the imaging timing. For example, the processing of FIG. 7B is performed to respective taken image data stored in the storage unit 14, whose psychological information, face flag and the face analysis result information are not stored there yet.

First, in Step F251, the storage unit 14 is instructed to read the taken image date to be processed.

Then, in Step F252, the subject information generating unit 12 is instructed to analyze the taken image in Step F252.

That is, the system controller 10 transfers the taken image data read by the storage unit 14 to the subject information generating unit 12. The subject information generating unit 12 performs analysis of the transferred taken image data in accordance with the instruction of by system controller 10. First, whether there is a face image in the image or not is analyzed. Then, the subject information generating unit 12 notifies the analysis result of whether there is a face image or not to the system controller 10.

The system controller 10, when receiving the notification of the presence of the face image, allows the process to proceed from Step F253 to F254, instructing the subject information generating unit 12 to generate subject information.

The subject information generating unit 12 generates information indicating that the face flag is on as subject information based on the fact that there is the face image in the image of the taken image data. The unit also analyzes the face image to generate face analysis result information. As described above, the face analysis result information is estimated information of expression, gender and the age bracket.

Subsequently, the system controller 10 instructs the storage unit 14 to read biosensor detection information corresponding to the taken image data to be processed at present in Step F255. In Step F256, the bio-information generating unit 5 is instructed to generate psychological information. That is, the system controller 10 transfers the biosensor detection information read by the storage unit 14 to the bio-information generating unit 5. The processing of estimating a psychological state is performed based on the biosensor detection information transferred to the bio-information generating unit 5 in accordance with the instruction of the system controller 10.

Then, the system controller 10 stores the subject information (face flag and face analysis result information) generated in the subject information generating unit 12 and the bio-information (psychological information) generated in the bio-information generating unit 5 in a state in which the information is associated with the taken image data in Step F257. That is, the bio-information generated by the bio-information generating unit 5 and the subject information generated in the subject information generating unit 12 are supplied in the storage unit 14, which is recorded in a state in which they are associated with the taken image data.

Accordingly, for example, the state in which the biosensor detection information, the psychological information, the face flag and the face analysis result information are associated with the taken image data as shown in FIG. 5 can be obtained.

On the other hand, when it is judged that there is not a face image as the analysis result of the taken image in Step F252, the system controller 10 allows the process to proceed to Step F258, instructing the subject information generating unit 12 to generate subject information indicating that the face flag is off.

Then, in Step F259, the face flag is transferred to the storage unit 14 to be stored in a state in which the flag is associated with the taken image data to be processed at present.

Also according to the processing in FIGS. 7A and 7B, when the face image is included in the taken image data, the storage state in which the biosensor detection information, the psychological information, the face flag, and the face analysis result information are associated with the taken image data as shown in FIG. 5 can be realized.

In the case that the bio-information generating unit 5 generates bio-information as shown in FIG. 6 regularly and stores the information in the storage unit 14, Step F203 and F204 in FIG. 7A will be the processing separated and independent from the processing at the time of imaging.

As an example of processing, it can be considered that generation/storing of subject information and generation/storing of psychological information are performed at further different timings.

[5. Image Search Processing Example I]

Since the bio-information and the subject information are stored in a state in which they are associated with the taken image data as described above, search processing by using the bio-information and the subject information becomes possible.

In FIG. 8, the processing of the system controller 10 as an image search processing example I is shown.

The system controller 10 detects presence/absence of a search trigger in Step F301.

For example, the system controller 10 recognizes an operation of instructing the start of searching by the user as the search trigger.

When there is the search trigger, the system controller 10 allows the process to proceed from Step F301 to F302, performing input processing of search conditions. For example, image display for inputting search conditions is performed on the display unit 2, and processing of allowing the user to select search conditions is performed.

In this case, search conditions can be designated based on items of bio-information indicating physical and psychological statuses of the user at the time of imaging and items of subject information.

For example, as the physical and psychological statuses of the user himself/herself, psychological conditions such as joyful, happy, anxious, exciting, tense, sad, calm and the like, or a cheerful state, a tired state, a sleepy state, a running state and the like are presented as candidates for search conditions, which will be selected by the user.

It is also preferable that the heart rate, the perspiration amount, brainwaves and the like are designated and that these numerical values or statuses are inputted as search conditions. For example, the user may designate a condition of "the heart rate is high" as a state in which the heart beats fast.

Concerning the subject information, the user can select an expression of a subject person, such as a smiling face, a sad face, an angry face, and a normal face. Further, the user can select the gender or the age bracket.

After the user inputs designation concerning the status of the user himself/herself at the time of imaging and designation concerning the subject information, the system controller 10 generates search conditions based on the input in Step F303. For example, the user designates "joyful" concerning the status of the user himself/herself, "smiling face" "women" and the like concerning the subject as the input of search conditions, these designated items are set as search conditions. It is also possible to perform designation such as "and/or" and the like concerning conditions designated by the user.

When the search conditions are set, the system controller 10 performs search processing in Step F304. That is, the system controller 10 searches the taken image data stored in the storage unit 14 by referring bio-information and subject information.

For example, in taken image data in which the face flag is on, bio-sensor detection information, psychological information and face analysis result information are confirmed, and corresponding taken image data is extracted.

In the case of the search conditions of "joyful" as the status of the user himself/herself and "smiling" and "women" as the subject are designated as the "and" condition, the taken image data corresponding to "joyful" as the psychological information and "smile" and "women" as the face analysis result information is extracted.

After the search processing ends, the system controller 10 performs search result display processing in Step F305. That is, the display unit 2 is instructed to execute search result display.

For example, when corresponding taken image data was not extracted, the display unit 2 is instructed to perform display of a message indicating that there is no corresponding data.

When one or plural taken image data are extracted, an image of the list thereof is displayed, and for example, processing of displaying one taken image is displayed, processing of displaying taken images in the order of time series of taken dates or processing of displaying taken images at random is performed in accordance with the designation of the user with respect to the list image.

It is also preferable to display the extracted taken images in order or at random, without displaying the list image.

[6. Image Search Processing Example II]

Next, as an image search processing example II, an example in which the designation of search conditions by the user is not inputted will be shown in FIG. 9.

The system controller 10 detects presence/absence of a search trigger in Step F401. When there is a search trigger, the system controller 10 allows the process to proceed from Step F401 to F402, determining the psychology of the user at the time of performing the search.

Accordingly, the system controller 10 instructs the bio-information generating unit 5 to generate psychological information of the user. The bio-information generating unit 5 performs processing of determining the psychology of the user by using detection information by the biosensor unit 4 at this time (or a certain period of time until the point) in accordance with the instruction of the system controller 10. The determination of psychological states such as joyful, happy, anxious, exciting, tense, sad, calm and the like is performed. The determination result is notified to the system controller 10.

Next, the system controller 10 generates search conditions in Step F403. In this case, search conditions are set in accordance with the psychological status of the user at the time.

In this case, when the user feels depressed, search conditions for images which make the user feel better, or when the user is nervous, search conditions for images which make the user relaxed are set. When the user is excited, search conditions for images which make the user calm are set. When the user feels happy, search conditions for images which make the user feel happier are set. Accordingly, the manner of setting search conditions can be variously considered.

For example, as search conditions which make the user feel better, conditions such as "joyful", "happy", or "exciting" are selected as the status of the user himself/herself at the time of imaging, or "smiling face" and the like is selected concerning the subject information, further, "sad face", "angry face" and the like are set as exclusion conditions.

As search conditions when calming the user in the excited state, conditions such as "calm" is selected as the status of the user himself/herself at the time of imaging, or a value indicating the calm state in a detected value of brainwaves is set. In addition, "normal expression" is selected concerning the subject information or search conditions excluding "angry" expressions are set. It can be considered that the age bracket of "children" is set.

When search conditions are set, the system controller 10 performs search processing in Step F404. That is, the system controller 10 searches taken image data stored in the storage unit 14 by referring bio-information or subject information.

After the search processing ends, the system controller 10 performs search result display processing in Step F405 and instructs the display unit 2 to display a search result.

According to the above processing, taken image data is extracted according to the mood of the user at the time of searching and is displayed.

The search trigger in Step F401 may be the operation of search instruction by the user, however, it is also preferable that the occurrence of a search trigger is determined when detecting a state in which user's psychology is depressed or excited by constantly determining the psychology of the user.

In Step F402, it can be considered to determine the psychology of a group of plural viewers, not the psychology determination of an individual user.

For example, in a group such as a family or friends, bio-sensor detection information or psychological information of respective persons are obtained, and group psychology is determine based on the information. For example, a state that they spend time pleasantly, a state that they are excited too much, a state that they are bored, a state that they are in an awkward mood and the like are determined. It is preferable to set search conditions in accordance with the determination and to perform searching and image display.

[7. Advantage of the Embodiments, Modification Examples, Extension Examples and Programs]

According to the above embodiments, bio-information of the user at the time of imaging (biosensor detection information and psychological information) and subject information (face flag and face analysis result information) are associated with taken image data and stored. At the time of searching, search conditions are generated by using the bio-information and the subject information to perform searching. The bio-information such as user's mood and the like at the time of imaging is used for generating search conditions.

Accordingly, image selection and display suitable for the viewer of images can be realized.

For example, according to the search processing example I of FIG. 8, face photographs taken in a desirable state for the user can be browsed. For example, it is possible to display face photographs in a state of excited psychology such as a case in which a face photograph of a woman recorded when the heart rate is more than 100 is searched or a case in which only photographs of smiling faces recorded when the heart rate is between 60 to 80 are extracted. Needless to say, the user as a viewer can execute arbitrary various searches by designating search conditions as biosensor detection information, psychological information and face analysis result information (expression, age bracket and gender).

According to the search processing example II of FIG. 9, the status of emotions and the like at the time of searching by a viewer (one or plural viewers) is estimated, and images corresponding to the psychological states and the like are presented, which are, for example, an image changing the viewer's state such as a photograph of a smiling face when the viewer is depressed, and an image maintaining the atmosphere of the place by displaying a photograph of a smiling face taken in an excited state when the viewer is excited, thereby turning around or calming the psychological state of a user or a group as viewers.

Particularly, to display an image taken in a calm state when the viewer is nervous at the time of browsing or to display an image taken in a happy mood and an image of a smiling face when the viewer is in a sad mood is considered to play a role of some type of phototherapy.

Particularly, in consideration of circumstances in which a great deal of taken image data is stored, the search described in the embodiment will be quite useful. For example, when user's action history of daily life is stored by performing automatic imaging every fixed time and a great deal of recording is performed, how to search a desired image at later point of time becomes important. In this point of view, proper image searching can be performed by applying the embodiment.

The invention is not limited to the embodiments and various modification examples or extension examples can be considered as the configuration examples or processing examples of the imaging apparatus 1.

The image storage processing apparatus and the image search apparatus according to an embodiment of the invention can be realized in apparatuses other than the imaging apparatus 1.

Examples of apparatus configurations as the image storage processing apparatus and the image search apparatus according to embodiments of the invention will be explained with reference to FIG. 10 to FIG. 14.

Figure 10:
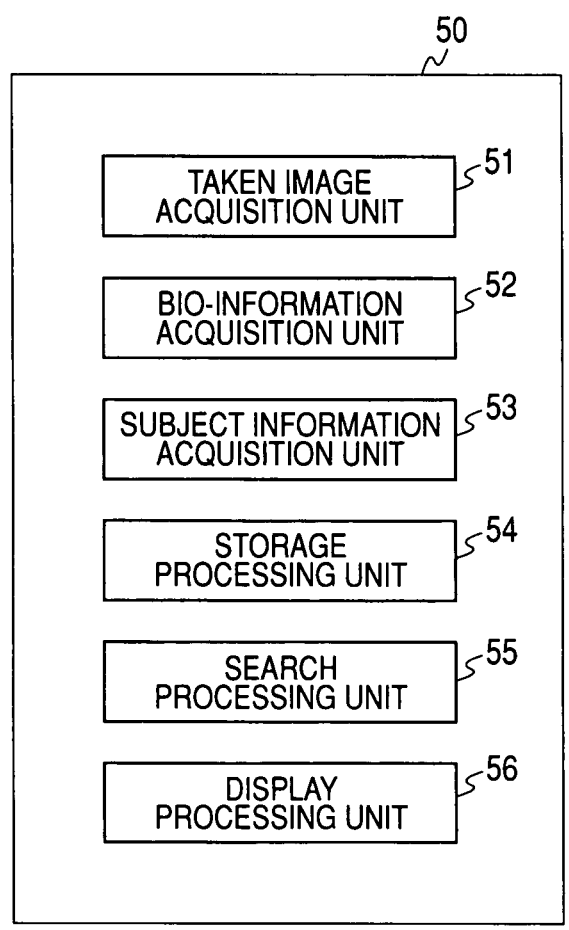
FIG. 10 is an explanatory diagram of a configuration example of an image storage processing apparatus and an image search apparatus according to an embodiment.

First, FIG. 10 shows a functional configuration of an apparatus 50 as the image storage processing apparatus and the image search apparatus according to an embodiment of the invention. The above imaging apparatus 1 also corresponds to the apparatus 50.

That is to say, a taken image acquisition unit 51, a bio-information acquisition unit 52, a subject information acquisition unit 53 and a storage processing unit 54, a search processing unit 55, and a display processing unit 56 are included.

The taken image acquisition unit 51 is a function of acquiring taken image data, for example, corresponding to the imaging unit 3 and the imaging control unit 6 in the imaging apparatus 1 of FIG. 2. The apparatus 50 does not have to have a function as a camera. For example, as the apparatus 50 which is connected to a camera, a receiving unit which receives taken image data transmitted by a cable or by wireless from the camera can be the taken image acquisition unit 51.

The bio-information acquisition unit 52 acquires user's bio-information. For example, the unit generates bio-information in a manner such as the biosensor unit 4 and the bio-information generating unit 5 in the imaging apparatus 1 in FIG. 2. However, it is also preferable that the bio-information acquisition unit 52 does not have the biosensor and like and receives bio-information from a separate biosensor or a bio-information generating unit.

The subject information acquisition unit 53 analyzes taken image data acquired in the taken image acquisition unit 51, generating subject information such as the face flag and the face analysis result information. In the above example, the subject information is acquired with respect to the face image, however, the target of the subject information is not limited to the face image.

The storage processing unit 54 performs processing of storing the taken image data acquired by the taken image acquisition unit 51, the bio-information acquired by the bio-information acquisition unit 52 and the subject information acquired by the subject information acquisition unit 53 in a state in which they are associated with one another. In the case of the imaging apparatus 1 of FIG. 2, the storage processing unit 54 is realized as storage processing in the storage unit 14 by the system controller 10.

The search processing unit 55 performs search processing of taken image data by using bio-information and subject information as search conditions. In the case of the imaging apparatus 1 in FIG. 2, the search processing unit 54 is realized as the search processing performed by the system controller 10.

The display processing unit 56 performs display processing of a search result of the search processing unit 55. In the case of the imaging apparatus 1 of FIG. 2, the display processing unit 54 is realized as the display control processing executed by the display unit 2 according to the instruction of the system controller 10.

The apparatus 50 is configured as the image storage processing apparatus according to an embodiment of the invention by including the taken image acquisition unit 51, the bio-information acquisition unit 52, the subject information acquisition unit 53 and the storage processing unit 54.

Also, the apparatus 50 is configured as the image search apparatus according to an embodiment of the invention by including the search processing unit 55 and the display processing unit 56 (further, the bio-information acquisition unit 52).

The apparatus 50 is specifically realized as an imaging apparatus such as a digital still camera or a video camera, an image processing apparatus, an image storage device and the like performing processing of images taken by the imaging apparatus. The image processing apparatus and the image storage device in this case can be realized as a function of a cellular phone device, a PDA, a personal computer, a video recorder, a video server and the like.

Figure 11:
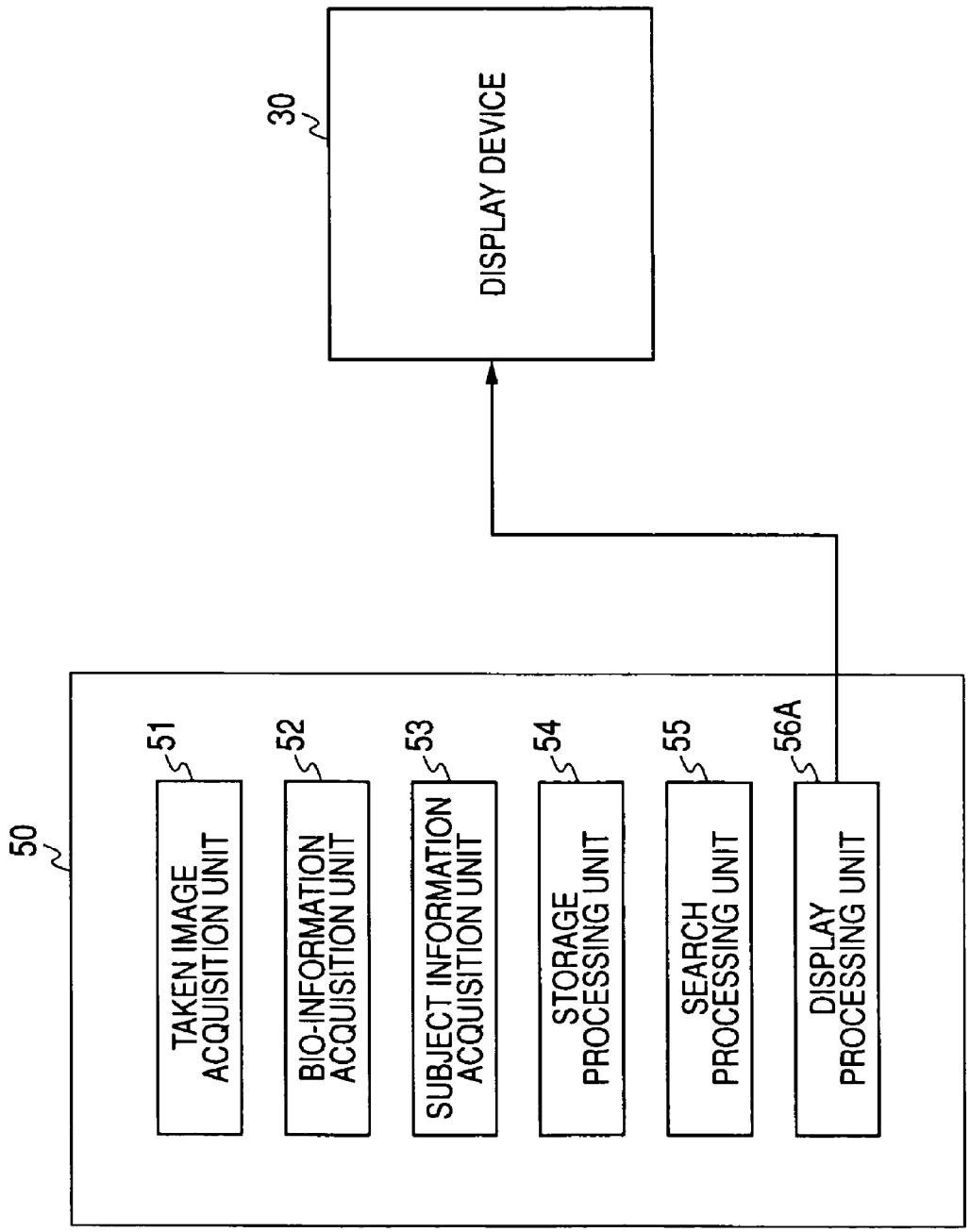
FIG. 11 is an explanatory diagram of a configuration example of an image storage processing apparatus and an image search apparatus according to an embodiment.

An apparatus 50 of FIG. 11 is also the apparatus 50 as the image storage processing apparatus and the image search apparatus according to an embodiment of the invention, which shows a configuration example in which display of search results are executed in a separate display device 30. For example, in the case of the imaging apparatus 1 not having the display function in the case of FIG. 1B, search result display can be realized according to the configuration.

A display processing unit 56A transmits taken image data as a search result to the display device 30 by a cable or by wireless, performing processing of displaying the data on the display device 30.

As the display device 30, various display devices can be considered, which are for example, a watch-type display device, a portable small-sized display device, equipment such as a cellular phone device and a PDA including a display panel, and stationary display devices such as a television monitor, a personal computer monitor.

Figure 12:
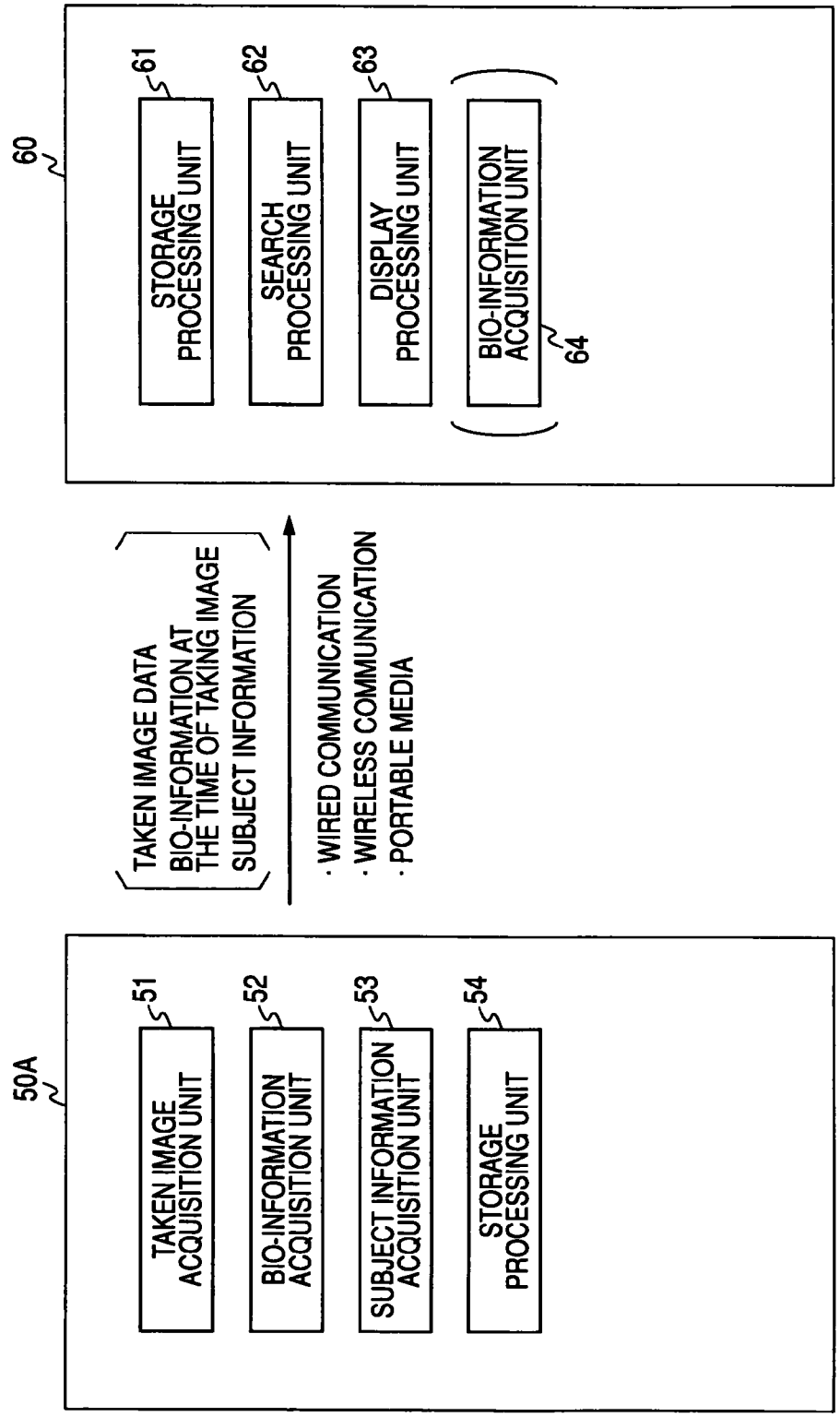
FIG. 12 is an explanatory diagram of a configuration example of an image storage processing apparatus and an image search apparatus according to an embodiment.

FIG. 12 shows an apparatus 50A as an image storage processing apparatus according to an embodiment of the invention and an apparatus 60 as an image search apparatus according to an embodiment of the invention, which have separate configurations.

The apparatus 50A is configured as the image storage processing apparatus according to an embodiment of the invention by including the taken image acquisition unit 51, the bio-information acquisition unit 52, the subject information acquisition unit 53 and the storage processing unit 54.

The apparatus 50A performs processing of storing taken image data acquired by the taken image acquisition unit 51, bio-information acquired by the bio-information acquisition unit 52 and subject information acquired by the subject information acquisition unit 53 through the processing of, for example, FIG. 3 or FIGS. 7A and 7B in a state in which the information is associated with one another.

In this case, the apparatus 50A can supply the taken image data, the bio-information at the time of imaging and the subject information stored by the storage processing unit 54 to the apparatus 60. For example, the taken image data, the bio-information at the time of imaging and the subject information are supplied to the apparatus 60 by wired communication, wireless transmission or the delivery of portable recording media.

The apparatus 60 is configured as the image search apparatus according to an embodiment of the invention by including a storage processing unit 61, a search processing unit 62, a display processing unit 63. The storage processing unit 61 stores taken image data, bio-information at the time of imaging and subject information supplied from the apparatus 50A in a recording medium.

The search processing unit 62 performs searching of the taken image data stored in the recording medium- by using the bio-information at the time of imaging and the subject information as search conditions. The display processing unit 63 performs display processing of a search result by the search processing unit 62. For example, the apparatus 60 performs search processing of FIG. 8.

The search processing unit 62 performs the search processing example II of FIG. 9 by including a bio-information acquisition unit 64 on the side of the apparatus 60, which enables the psychological status and the like of the viewer at the time of searching to be reflected on search conditions.

The apparatus 50A in FIG. 12 is specifically realized as an imaging apparatus such as a digital still camera or a video camera, an image processing apparatus, an image storage device and the like performing processing of images taken by the imaging apparatus. The image processing apparatus and the image storage device can be realized as a cellular phone device, a PDA, a personal computer, a video recorder, a video server and the like.

The apparatus 60 can be realized as the image processing apparatus and the image storage apparatus, which are specifically, a cellular phone device, a PDA, a personal computer, a video recorder, a video server and the like.

Figure 13:
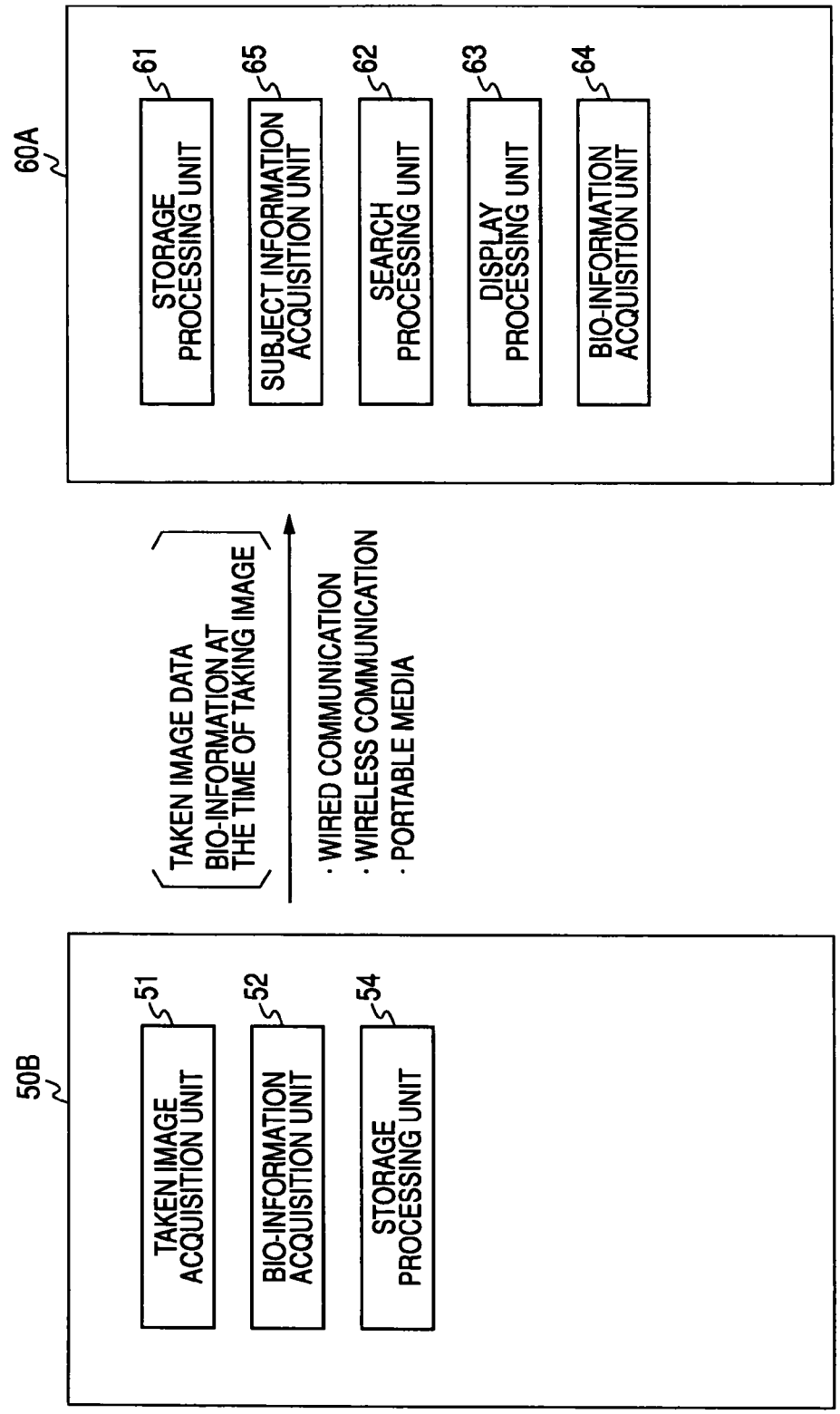
FIG. 13 is an explanatory diagram of a configuration example of an image storage processing apparatus and an image search apparatus according to an embodiment.

FIG. 13 shows apparatuses 50B, 60A, which shows an example in which the image storage processing apparatus and the image search apparatus according to an embodiment of the invention are realized as the apparatus 60A.

In this case, the apparatus 50B is, for example, an imaging apparatus, performing processing of storing taken image data acquired by the taken image acquisition unit 51 and biosensor detection information acquired by the bio-information acquisition unit 52 through the processing of FIG. 7A in a state in which the information is associated with each other.

In this case, the apparatus 50B can supply the taken image data and biosensor detection information at the time of imaging stored by the storage processing unit 54 to the apparatus 60A. For example, the taken image data and the biosensor detection information are supplied to the apparatus 60A by wired communication, wireless transmission or the delivery of portable recording media.

The apparatus 60A includes the storage processing unit 61, the search processing unit 62, the display processing unit 63, the bio-information acquisition unit 64 and a subject information acquisition unit 65. The storage processing unit 61 stores the taken image data and the biosensor detection information supplied from the apparatus 50B in a recording medium.

The bio-information acquisition unit 64, the subject information acquisition unit 65 and the storage processing unit 61 perform processing of, for example, FIG. 7B, which generates bio-information (psychological information) and subject information (face flag, face analysis result information) with respect to the taken image data stored in the recording medium and stores them in the recording medium in a state in which the information is associated with the taken image data.

The search processing unit 62 performs searching of the taken image data stored in the recording medium by using the bio-information at the time of imaging and subject information as search conditions. The display processing unit 63 performs display processing of a search result of the search processing unit 62.

In this case, the apparatus 60A can perform search processing of FIG. 8 or FIG. 9.

The apparatus 60A in FIG. 13 can be realized as an image processing apparatus, an image storage device, and an image search device. Specifically, it is realized as a cellular phone device, a PDA, a personal computer, a video recorder, a video server and the like.

It is also preferable that image analysis is performed on the side of the apparatus 50B, taken image data is stored so that the data is associated with the face flag and the taken image data including the face flag is supplied to the apparatus 60A. In this case, on the side of the apparatus 60A, it is preferable that processing of adding subject information (face analysis result information) concerning taken image data in which the face flag is on is performed.

Figure 14:
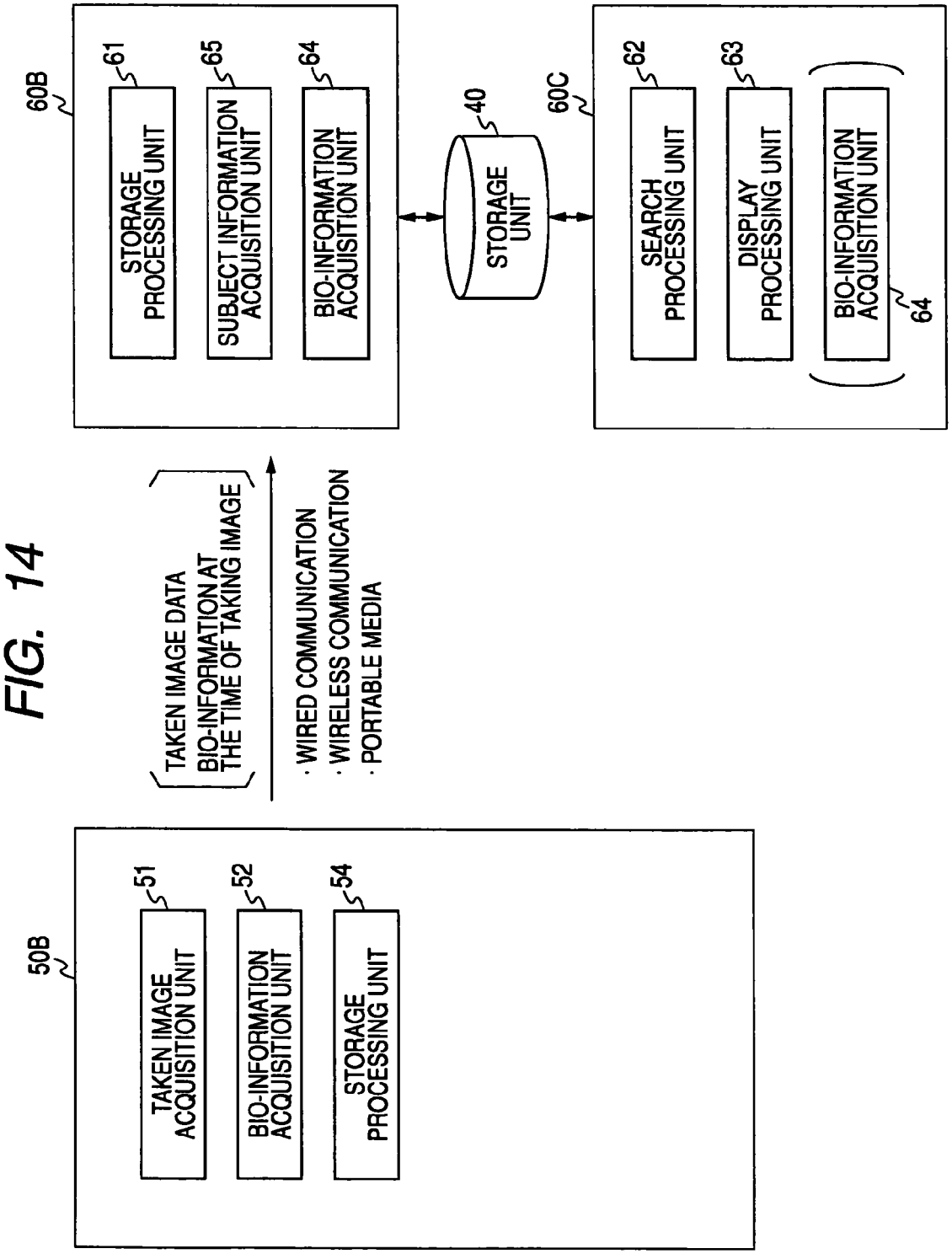
FIG. 14 is an explanatory diagram of a configuration example of an image storage processing apparatus and an image search apparatus according to an embodiment.

FIG. 14 shows the apparatus 50B, an apparatus 60B and an apparatus 60C, which is an example in which the apparatus 60B corresponds to the image storage processing apparatus according to an embodiment of the invention, and the apparatus 60C corresponds to the image search apparatus according to an embodiment of the invention. The apparatuses 60B, 60C can access to a storage unit 40.

In this case, the apparatus 50B is, for example, an imaging apparatus, performing processing of storing taken image data acquired by the taken image acquisition unit 51 and biosensor detection information acquired by the bio-information acquisition unit 52 through the processing of FIG. 7A in a state in which they are associated with each other.

The apparatus 50B supplies the taken image data and the biosensor detection information at the time of imaging stored by the storage processing unit 54 to the apparatus 60B. For example, the taken image data, the biosensor detection information at the time of imaging are supplied to the apparatus 60B by wired communication, wireless transmission or the delivery a portable recording medium.

The apparatus 60B includes the storage processing unit 61, the bio-information acquisition unit 64 and the subject information acquisition unit 65.

The storage processing unit 61 stores taken image data and the biosensor detection information supplied from the apparatus 50B in a recording medium.

The bio-information acquisition unit 64, the subject information acquisition unit 65 and the storage processing unit 61 perform the processing of, for example, FIG. 7B, which generates bio-information (psychological information) and subject information (face flag, face analysis result information) with respect to the taken image data stored in the recording medium and stores them in the storage unit 40 in a state in-which the information is associated with the taken image data.

The apparatus 60C includes the search processing unit 62 and the display processing unit 63.

The search processing unit 62 performs searching of the taken image data stored in the storage unit 40 by using the bio-information at the time of imaging and subject information as search conditions. The display processing unit 63 performs display processing of a search result of the search processing unit 62. For example, the apparatus 60C performs searching processing of FIG. 8.

The search processing unit 62 performs the search processing example II of FIG. 9 by including the bio-information acquisition unit 64 also on the side of the apparatus 60C, which enables the psychological status and the like of the viewer at the time of searching to be reflected on search conditions.

The apparatuses 60B, 60C in FIG. 14 can be realized as apparatuses having functions as an image processing apparatus, the image storage device, and the image search device, which are specifically, a cellular phone device, a PDA, a personal computer, a video recorder, a video server and the like.

It is also preferable that image analysis is performed on the side of the apparatus 50B and taken image data is stored so that the data is associated with the face flag and the taken image data including the face flag is supplied to the apparatus 60B. In this case, on the side of the apparatus 60B, it is preferable that processing of adding subject information (face analysis result information) concerning taken image data in which the face flag is on is performed.

The communication between apparatuses in FIG. 11 to FIG. 14 can be the communication through networks such as Internet, a cellular phone communication network, a PHS communication network, an ad hoc network, or a LAN.

A program according to embodiments is a program allowing the image storage processing in FIG. 3 or FIGS. 7A and 7B to be executed by a microcomputer (calculation processing unit) in an imaging apparatus, a personal computer, a cellular phone device, a PDA, a video server, a video recorder and the like. A program according to embodiments is a program allowing the image search processing of FIG. 8 or FIG. 9 to be executed by a microcomputer (calculation processing unit) in these devices.

These programs can be recorded in advance in a HDD as a recording medium included in equipment such as a personal computer, an imaging apparatus, or a ROM in a microcomputer having a CPU, a flash memory and the like.

These programs can be also temporarily or permanently stored (recorded) in removable recording media such as a flexible disc, a CD-ROM (Compact. Disc Read Only Memory), MO(Magnet Optical) disc, a DVD (Digital Versatile Disc), a Blu-ray disc, a magnetic disc, a semiconductor memory, and a memory card. The removable recording media can be provided as so-called packaged software.

The programs can be also installed from removable recording media to a personal computer and the like, in addition, can be downloaded from download sites through networks such as a LAN (Local Area Network) or Internet.

It should be understood by those skilled in the art that various modifications, combinations, sub-combinations and alterations may occur depending on design requirements and other factors insofar as they are within the scope of the appended claims or the equivalents thereof.

What is claimed is:

1. An image storage processing apparatus, comprising:
    an image acquisition means for acquiring taken image data imaged at an imaging apparatus unit;
    a user information acquisition means for acquiring first user information relating to at least one first physical measurement taken from a body of a user of the imaging apparatus unit at a time of taking an image and thereby generating the taken image data, the user of the imaging apparatus unit being a first user;
    a subject information acquisition means for acquiring, as subject information, an image analysis result of analyzing the taken image data;
    a storage processing means for recording the taken image data acquired by the image acquisition means, the first user information acquired by the user information acquisition means, and the subject information acquired by the subject information acquisition means in at least one recording medium in such a manner that the taken image data is associated with the first user information and the subject information; and
    a search processing means for generating one or more search conditions using second user information relating to at least one second physical measurement taken from a body of a second user different from the first user, the at least one second physical measurement being taken at a time of searching, and for using the one or more search conditions to search for image data stored in association with corresponding user information and/or subject information that matches the one or more search conditions, wherein the search processing means is configured to generate the one or more search conditions in response to a determination that the second user is in one of one or more designated psychological states.

2. The image storage processing apparatus according to claim 1, further comprising the imaging apparatus unit, wherein the imaging apparatus unit is integral with the image storage processing apparatus, and wherein the image acquisition means is configured to acquire the taken image data by an imaging operation in the imaging apparatus unit.

3. The image storage processing apparatus according to claim 1, wherein the imaging apparatus unit is an external imaging apparatus unit, and the image acquisition means is configured to acquire the taken image data by an imaging operation in the external imaging apparatus unit.

4. The image storage processing apparatus according to claim 1, wherein the user information acquisition means is configured to use one or more sensors to acquire biosensor detection information as the first user information.

5. The image storage processing apparatus according to claim 1, wherein the user information acquisition means is configured to generate psychological information of the first user as the first user information by using biosensor detection information.

6. The image storage processing apparatus according to claim 1, wherein the subject information acquisition means is configured to analyze whether a face image of a person is included in the taken image data to obtain face presence information, and wherein the subject information comprises the face presence information.

7. The image storage processing apparatus according to claim 1, wherein the subject information acquisition means is configured to analyze a face image of a person in the taken image data to obtain face analysis result information, and wherein the subject information comprises the face analysis result information.

8. The image storage processing apparatus according to claim 7, wherein the face analysis result information comprises information indicating expression, gender, or an age bracket.

9. The image storage processing apparatus according to claim 1, further comprising:
an output processing means for performing output processing of a search processing result by the search processing means.

10. The image storage processing apparatus according to claim 9, wherein the search processing means is further configured to generate the one or more search conditions based at least in part on user input.

11. The image storage processing apparatus of claim 1, wherein the second user information relates to a plurality of physical measurements taken respectively from a plurality of users, the plurality of users comprising the second user.

12. An image search apparatus, comprising:
a user information acquisition means for acquiring current user information relating to at least one current physical measurement taken from a body of a first user;
a search processing means for generating one or more search conditions based at least in part on the current user information and for using the one or more search conditions to search at least one recording medium to identify taken image data that is stored in association with prior user information and/or subject information that matches the one or more search conditions, wherein:
the search processing means is configured to generate the one or more search conditions in response to a determination that the first user is in one of one or more designated psychological states;
the taken image data was imaged by an imaging apparatus unit used by a second user different from the first user;
the prior user information relates to at least one prior physical measurement taken from a body of the second user at a time of taking an image and thereby generating the taken image data; and
the subject information comprises an image analysis result of analyzing the taken image data; and
an output processing means for performing output processing of a search processing result by the search processing means.

13. The image search apparatus according to claim 12, wherein the search processing means is further configured to use user input for generating the one or more search conditions.

14. An image storage processing method, comprising acts of:
acquiring taken image data imaged at an imaging apparatus unit;
acquiring first user information relating to at least one first physical measurement taken from a body of a user of the imaging apparatus unit at a time of taking an image and thereby generating the taken image data, the user of the imaging apparatus unit being a first user;
acquiring, as subject information, an image analysis result of analyzing the taken image data;
using at least one processor to record the taken image data, the first user information, and the subject information in at least one recording medium in such a manner that the taken image data is associated with the first user information and the subject information;
generating one or more search conditions using second user information relating to at least one second physical measurement taken from a body of a second user different from the first user, the at least one second physical measurement being taken at a time of searching, wherein the act of generating the one or more search conditions is performed in response to a determination that the second user is in one of one or more designated psychological states; and
using the one or more search conditions to search for image data stored in association with corresponding user information and/or subject information that matches the one or more search conditions.

15. An image search method, comprising acts of:
acquiring current user information relating to at least one current physical measurement taken from a body of a first user;
using, in response to a determination that the first user is in one of one or more designated psychological states, at least one processor to generate one or more search conditions based at least in part on the current user information and to use the one or more search conditions to search at least one recording medium to identify taken image data that is stored in association with prior user information and/or subject information that matches the one or more search conditions, wherein:
the taken image data was imaged by an imaging apparatus unit used by a second user different from the first user;
the prior user information relates to at least one prior physical measurement taken from a body of the second user at a time of taking an image and thereby generating the taken image data; and
the subject information comprises an image analysis result of analyzing the taken image data; and
performing output processing of a search result.

16. The image search method of claim 15, wherein the current user information comprises current psychological information indicative of a current psychological state of the first user, and wherein the act of acquiring the current user information comprises:
in response to the determination that the first user is in one of one or more designated psychological states, using at least one biosensor to take the at least one current physical measurement from the body of the first user; and
generating the current psychological information based at least in part on the at least one current physical measurement taken from the body of the first user.

17. The image search method of claim 16, wherein the act of performing output processing of the search result comprises an act of displaying the search result to the first user, and wherein the one or more search conditions are generated to identify one or more images likely to influence the current psychological state of the first user.

18. The image search method of claim 15, wherein the at least one processor is configured to generate the one or more search conditions in response to a determination that the first user is in a state of being depressed or a state of being excited.

19. At least one non-transitory recording medium which records a program allowing an information processing apparatus to execute the steps of:
acquiring taken image data imaged at an imaging apparatus unit;
acquiring first user information relating to at least one first physical measurement taken from a body of a user of the imaging apparatus unit at a time of taking an image and thereby generating the taken image data, the user of the imaging apparatus unit being a first user;
acquiring, as subject information, an image analysis result of analyzing the taken image data;
recording the taken image data, the first user information, and the subject information in at least one recording medium in such a manner that the taken image data is associated with the first user information and the subject information;
generating one or more search conditions using second user information relating to at least one second physical measurement taken from a body of a second user different from the first user, the at least one second physical measurement being taken at a time of searching, wherein the program allows the information processing apparatus to execute the step of generating the one or more search conditions in response to a determination that the second user is in one of one or more designated psychological states; and
using the one or more search conditions to search for image data stored in association with corresponding user information and/or subject information that matches the one or more search condition.

20. At least one non-transitory recording medium which records a program allowing an information processing apparatus to execute the steps of:
acquiring current user information relating to at least one current physical measurement of taken from a body of a first user;
generating one or more search conditions based at least in part on the current user information and using the one or more search conditions to search at least one recording medium to identify taken image data that is stored in association with prior user information and/or subject information that matches the one or more search conditions, wherein:
the program allows the information processing apparatus to execute the step of generating the one or more search conditions in response to a determination that the first user is in one of one or more designated psychological states;
the taken image data was imaged by an imaging apparatus unit used by a second user different from the first user;
the prior user information relates to at least one prior physical measurement taken from a body of the second user at a time of taking an image and thereby generating the taken image data; and
the subject information comprises an image analysis result of analyzing the taken image data; and
performing output processing of a search result.

21. An image storage processing apparatus, comprising:
an image acquisition unit configured to acquire taken image data imaged at an imaging apparatus unit;
a user information acquisition unit configured to acquire first user information relating to at least one first physical measurement taken from a body of a user of the imaging apparatus unit at a time of taking an image and thereby generating the taken image data, the user of the imaging apparatus unit being a first user;
a subject information acquisition unit configured to acquire, as subject information, an image analysis result of analyzing the taken image data;
a storage processing unit configured to record the taken image data, the first user information, and the subject information in at least one recording medium in such a manner that the taken image data is associated with the first user information and the subject information; and
a search processing unit for generating one or more search conditions using second user information relating to at least one second physical measurement taken from a body of a second user different from the first user, the at least one second physical measurement being taken at a time of searching, and for using the one or more search conditions to search for image data stored in association with corresponding user information and/or subject information that matches the one or more search conditions, wherein the search processing unit is configured to generate the one or more search conditions in response to a determination that the second user is in one of one or more designated psychological states.

22. An image search apparatus, comprising:
a user information acquisition unit configured to acquire current user information relating to at least one current physical measurement of taken from a body of a first user;
a search processing unit configured to generate one or more search conditions based at least in part on the current user information and to use the one or more search conditions to search at least one recording medium to identify taken image data that is stored in association with prior user information and/or subject information that matches the one or more search conditions, wherein:
the search processing unit is configured to generate the one or more search conditions in response to a determination that the first user is in one of one or more designated psychological states;
the taken image data was imaged by an imaging apparatus unit used by a second user different from the first user;
the prior user information relates to at least one prior physical measurement taken from a body of the second user at a time of taking an image and thereby generating the taken image data, and
the subject information comprises an image analysis result of analyzing the taken image data; and
an output processing unit configured to perform output processing of a search processing result by the search processing unit.

* * * * *